(12) United States Patent
Hancock et al.

(10) Patent No.: US 11,382,691 B2
(45) Date of Patent: Jul. 12, 2022

(54) ELECTROSURGICAL INSTRUMENT

(71) Applicant: CREO MEDICAL LIMITED, Chepstow (GB)

(72) Inventors: Christopher Paul Hancock, Bath (GB); Julian Mark Ebbutt, Chepstow (GB); Louis Turner, Chepstow (GB); Simon Meadowcroft, Chippenham (GB)

(73) Assignee: CREO MEDICAL LIMITED, Chepstow (GB)

( * ) Notice: Subject to any disclaimer, the term of this patent is extended or adjusted under 35 U.S.C. 154(b) by 821 days.

(21) Appl. No.: 15/942,141

(22) Filed: Mar. 30, 2018

(65) Prior Publication Data
US 2018/0280084 A1    Oct. 4, 2018

(30) Foreign Application Priority Data
Mar. 30, 2017    (GB) ...................................... 1705171

(51) Int. Cl.
*A61B 18/12*    (2006.01)
*A61B 18/18*    (2006.01)
(Continued)

(52) U.S. Cl.
CPC ...... *A61B 18/1815* (2013.01); *A61B 18/1445* (2013.01); *A61B 17/320068* (2013.01); *A61B 18/1206* (2013.01); *A61B 18/16* (2013.01); *A61B 2017/320082* (2017.08); *A61B 2018/0063* (2013.01); *A61B 2018/00077* (2013.01);
(Continued)

(58) Field of Classification Search
CPC . A61B 18/1206; A61B 18/1445; A61B 18/16; A61B 18/1815; A61B 2018/1452; A61B 2018/1455; A61B 2018/165; A61B 2018/1823; A61B 2018/183; A61B 2018/1876; A61B 2018/1892
See application file for complete search history.

(56) References Cited

U.S. PATENT DOCUMENTS 6,585,735 B1    7/2003    Frazier et al.
7,534,243 B1 *  5/2009    Chin ................ A61B 17/00008
                                                              606/41
(Continued)

FOREIGN PATENT DOCUMENTS

EP           2 233 098 A1    9/2010
WO    WO 2015/097472 A1    7/2015

OTHER PUBLICATIONS

Written Opinion of the International Searching Authority issued in International Application No. PCT/EP2018/058116 dated Aug. 24, 2018.

*Primary Examiner* — Daniel W Fowler
(74) *Attorney, Agent, or Firm* — ArentFox Schiff LLP

(57) ABSTRACT

An electrosurgical vessel sealing device that can seal biological vessels using a confined microwave field that yields a well-defined seal location with low thermal margin. The device comprises a pair of jaws that are movable relative to each other to grip biological tissue. A blade for cutting the gripped tissue is slidable between the jaws. A coplanar microstrip antenna is mounted on the inner surface of one or both of the pair of jaws to emit microwave energy into the gap therebetween. The device may comprise a separate dissector element to enable fine tissue cutting and dissection to be performed.

21 Claims, 15 Drawing Sheets

(51) Int. Cl.
   *A61B 18/14* (2006.01)
   *A61B 18/00* (2006.01)
   *A61B 18/16* (2006.01)
   *A61B 17/32* (2006.01)

(52) U.S. Cl.
   CPC ............... *A61B 2018/00083* (2013.01); *A61B 2018/00095* (2013.01); *A61B 2018/00178* (2013.01); *A61B 2018/00196* (2013.01); *A61B 2018/00345* (2013.01); *A61B 2018/00404* (2013.01); *A61B 2018/00589* (2013.01); *A61B 2018/00595* (2013.01); *A61B 2018/00601* (2013.01); *A61B 2018/00607* (2013.01); *A61B 2018/00982* (2013.01); *A61B 2018/00994* (2013.01); *A61B 2018/126* (2013.01); *A61B 2018/1452* (2013.01); *A61B 2018/1455* (2013.01); *A61B 2018/162* (2013.01); *A61B 2018/165* (2013.01); *A61B 2018/183* (2013.01); *A61B 2018/1823* (2013.01); *A61B 2018/1876* (2013.01); *A61B 2018/1892* (2013.01)

(56) References Cited

U.S. PATENT DOCUMENTS

| | | |
|---|---|---|
| 2003/0055417 A1 | 3/2003 | Truckai et al. |
| 2003/0130575 A1* | 7/2003 | Desai ............ A61K 9/0031 600/417 |
| 2003/0144652 A1* | 7/2003 | Baker ............ A61B 18/1442 606/28 |
| 2004/0254606 A1* | 12/2004 | Wittenberger ....... A61B 17/122 606/205 |
| 2005/0033278 A1* | 2/2005 | McClurken ........ A61B 18/1445 606/41 |
| 2005/0203499 A1* | 9/2005 | Pendekanti ............ A61N 7/02 606/27 |
| 2008/0294222 A1* | 11/2008 | Schechter ........ A61B 18/1445 607/50 |
| 2008/0319442 A1* | 12/2008 | Unger ............ A61B 18/1445 606/48 |
| 2010/0249769 A1 | 9/2010 | Nau, Jr. et al. |
| 2012/0059371 A1* | 3/2012 | Anderson ........... A61B 18/085 606/45 |
| 2012/0253344 A1 | 10/2012 | Dumbauld et al. |
| 2012/0330310 A1 | 12/2012 | Takashino |
| 2013/0103030 A1* | 4/2013 | Garrison ........... A61B 18/1442 606/42 |
| 2013/0144284 A1 | 6/2013 | Behnke, II et al. |
| 2013/0274733 A1 | 10/2013 | Hancock |
| 2013/0289557 A1 | 10/2013 | Hancock et al. |
| 2014/0100569 A1 | 4/2014 | Lawes et al. |
| 2015/0088128 A1 | 3/2015 | Couture |
| 2016/0235475 A1 | 8/2016 | Brustad et al. |
| 2016/0331455 A1 | 11/2016 | Hancock et al. |
| 2017/0156791 A1* | 6/2017 | Govari ............ A61B 5/4836 |

* cited by examiner

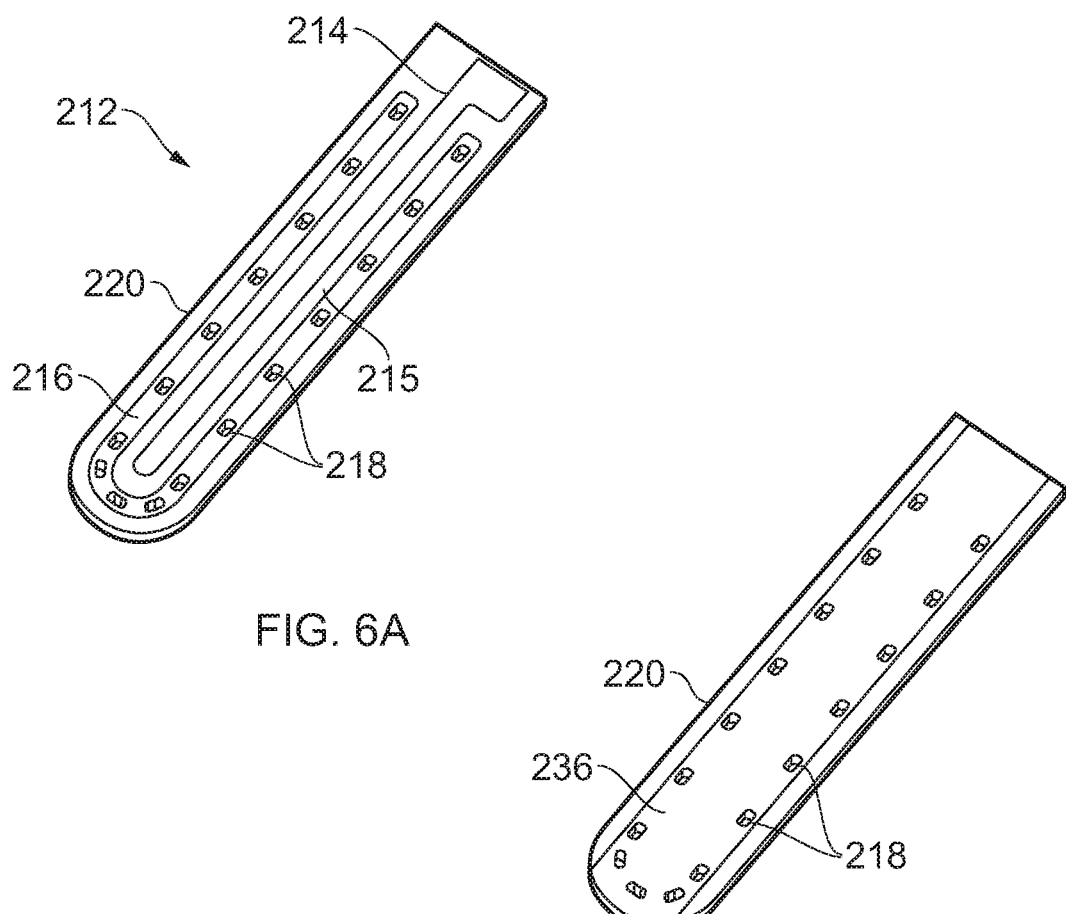

ELECTROSURGICAL INSTRUMENT

FIELD OF THE INVENTION

The invention relates to an electrosurgical vessel sealer for grasping biological tissue and for delivering microwave energy into the grasped tissue to coagulate or cauterise or seal the tissue. In particular, the vessel sealer may be used to apply pressure to close one or more blood vessels before applying electromagnetic radiation (preferably microwave energy) to seal the blood vessel(s). The vessel sealer may also be arranged to divide, e.g. separate or cut, the vessel of surrounding tissue after coagulation or sealing, e.g. using radiofrequency (RF) energy or a mechanical cutting element, such as a blade. The invention may be applied to a vessel sealer for use in laparoscopic surgery or open surgery.

BACKGROUND TO THE INVENTION

Forceps capable of delivering heat energy into grasped biological tissue are known [1]. For example, it is known to deliver radiofrequency (RF) energy from a bipolar electrode arrangement in the jaws of the forceps [2,3]. The RF energy may be used to seal vessel by thermal denaturation of extracellular matrix proteins (e.g. collagen) within the vessel wall. The heat energy may also cauterise the grasped tissue and facilitate coagulation.

Such devices typically find application on the end of minimal invasive surgical laparoscopic tools but can equally find use in other clinical procedural areas such as gynaecology, endourology, gastrointestinal surgery, ENT procedures, etc. Depending on the context of use, these device can have differing physical construction, size, scale and complexity.

For example, a gastrointestinal instrument might be nominally of 3 mm diameter mounted on to the end of a very long flexible shaft. In contrast, a laparoscopic instrument may be used on the end of an industry standard nominal 5 mm or 10 mm diameter rigid or steerable steel shaft.

Current examples of minimally invasive device that are capable of dissecting body tissue at the same time as achieving haemostasis include the LigaSure vessel sealing technology manufactured by Covidien, and the Thunderbeat platform from Olympus. The LigaSure system is a bipolar forceps arrangement in which current is delivered to seal tissue while pressure is applied. The Thunderbeat platform simultaneously delivers thermal energy generated using an ultrasonic source, and bipolar electrical energy.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave energy into tissue grasped between the jaws of the forceps.

WO 2015/097472 describes electrosurgical forceps in which one or more pairs of non-resonant unbalanced lossy transmission line structure are arranged on the inner surface of a pair of jaws.

SUMMARY OF THE INVENTION

At its most general, the present invention provides a vessel sealer that can seal biological vessels using a confined microwave field that can yield a well-defined seal location with low thermal margin. Moreover, the vessel sealer may provide auxiliary functionality, such as a blade to assist vessel dividing or a separate dissector element to enable fine tissue cutting and dissection to be performed. With these auxiliary functions, fewer device interchanges may be needed during a procedure.

The vessel sealer disclosed herein may be used in any type of surgical procedure, but it is expected to find particular utility for non-invasive or minimally invasive procedures. For example, the device may be configured to be introduced to a treatment site through an instrument channel of a surgical scoping device, such as a laparoscope or an endoscope.

According to a first aspect of the present invention, there is provided an electrosurgical vessel sealer comprising: an instrument shaft comprising a coaxial transmission line for conveying microwave electromagnetic (EM) energy; a distal end assembly arranged at a distal end of the instrument shaft to receive the microwave EM energy from the instrument shaft, the distal end assembly comprising: a pair of jaws that are movable relative to each other to open and close a gap between opposing inner surfaces thereof; and a blade for cutting through biological tissue, wherein the pair of jaws comprise an energy delivery structure arranged to emit the microwave EM energy into the gap between the opposing inner surfaces, wherein the energy delivery structure is arranged to confine an emitted microwave field substantially within a region between the pair of jaws, and wherein the blade is slidably disposed within the distal end assembly to be movable through the region between the pair of jaws. In this aspect, the energy delivery structure in the pair of jaws operates to provide a localised vessel seal for a biological vessel gripped between the jaws, and the blade is operable to cut through the seal and divide the vessel.

In use, the vessel sealer of the first aspect may thus perform vessel sealing and vessel dividing. Vessel sealing is typically the application of pressure to squash the walls of a biological vessel together, followed by the application of some form of thermal energy. In the invention, the thermal energy is applied by dielectric heating the gripped tissue using the microwave EM energy. The applied electro-mechanical energy disrupts/denatures the tissue cells and forms an amalgam of collagen predominant in vessel walls, which effectively bonds the vessel walls together. With time, post operatively, cellular recovery and regrowth occurs to reinforce the seal further. Vessel dividing is a process of cutting through a continuous biological vessel to separate it into two pieces. It is normally performed after a vessel is first sealed. In this aspect of the invention, vessel dividing is performed by the blade, which is discussed in more detail below.

Herein, the terms "proximal" and "distal" refer to the ends of the energy conveying structure further from and closer to the treatment site respectively. Thus, in use the proximal end is closer to a generator for providing the RF and/or microwave energy, whereas the distal end is closer to the treatment site, i.e. the patient.

The term "conductive" is used herein to mean electrically conductive, unless the context dictates otherwise.

The term "longitudinal" used below refers to the direction along the instrument channel parallel to the axis of the coaxial transmission line. The term "lateral" refers to a direction that is perpendicular to the longitudinal direction. The term "inner" means radially closer to the centre (e.g. axis) of the instrument channel. The term "outer" means radially further from the centre (axis) of the instrument channel.

The term "electrosurgical" is used in relation an instrument, apparatus or tool which is used during surgery and which utilises radiofrequency (RF) electromagnetic (EM)

energy and/or microwave EM energy. Herein, RF EM energy may mean a stable fixed frequency in a range 10 kHz to 300 MHz, preferably in a range from 100 kHz to 5 MHz, and more preferably in a range from 360 to 440 kHz. The microwave EM energy may mean electromagnetic energy having a stable fixed frequency in the range 300 MHz to 100 GHz. The RF EM energy should have a frequency high enough to prevent the energy from causing nerve stimulation. In use, the magnitude of the RF EM energy and the duration for which it is applied may be selected to prevent the energy from causing tissue blanching or unnecessary thermal margin or damage to the tissue structure. Preferred spot frequencies for the RF EM energy include any one or more of: 100 kHz, 250 kHz, 400 kHz, 500 kHz, 1 MHz, 5 MHz. Preferred spot frequencies for the microwave EM energy include 915 MHz, 2.45 GHz, 5.8 GHz, 14.5 GHz, 24 GHz. 5.8 GHz may be preferred.

The energy delivery structure may comprise a microwave radiator element disposed on the inner surface of one or both of the pair of jaws. For example, the pair of jaws may comprise an active jaw having the energy delivery structure mounted therein, and a passive jaw which does not receive a microwave EM energy feed. Alternatively, each jaw in the pair of jaws may have a respective energy delivery structure mounted therein. In this scenario, the distal end assembly may includes a power splitter for dividing the microwave EM energy received from the coaxial transmission line between the respective energy delivery structures. In a further example, the energy delivery structure may have components that are divided between the pair of jaws, so that the pair of jaws in combination provide a microwave radiator element.

The microwave radiator element may comprise a coplanar microstrip antenna mounted on the inner surface of one or both of the pair of jaws. In one embodiment, the coplanar microstrip antenna may be mounted on an active jaw and the opposing jaw may be a passive jaw. The inner surface of the passive jaw at the gap may comprise a resilient deformable layer of electrically insulating material, e.g. silicone rubber or the like. The layer of electrically insulating material may provide a thermal barrier to inhibit propagation of heat beyond the jaws. In some cases, the deformable layer may assist in providing a substantially constant clamping force along the length of the pair of jaws.

The coplanar microstrip antenna may comprise a planar dielectric substrate having a top surface that is exposed at the gap between the opposing inner surfaces, and an under surface on an opposite side of the planar dielectric substrate from the top surface. The dielectric substrate may be made from a suitable ceramic. It may be mounted, e.g. bonded or otherwise affixed, to the active jaw. A ground conductor layer may be provided on the under surface. This may be a layer of metallisation, e.g. of copper, silver, gold or the like. On the top surface of the dielectric substrate, there may be provided a ground conductive strip that is electrically connected to the ground conductor layer, and an active conductive strip that is spaced from the ground conductive strip. The ground conductor may be electrically connected to an outer conductor of the coaxial transmission line. The active conductive strip may be connected to an inner conductor of the coaxial transmission line. The active conductive strip and the ground conductive strip may be positioned to have a uniform closest spacing within the region between the pair of jaws. The closest spacing between the active conductive strip and the ground conductive strip is the region when the emitted microwave field will be at its strongest. Accordingly, a geometry for the active conductive strip and the ground conductive strip can be selected that confines the field within the region between the jaws.

In one example, the active conductive strip may be an elongate longitudinally extending finger electrode. The ground conductive strip comprise one or more elongate portions that flank the finger electrode whereby the closest spacing comprises a elongate longitudinally extending portion along the inner surface of the pair of jaws. The ground conductive strip may flank both sides of the finger electrode. In one example, the ground conductive strip may be a U-shaped element that flanks both sides of the finger electrode and surrounds its distal end. In this example the field may be confined primarily within a region lying inwardly of the U-shaped element.

The ground conductive strip may be electrically connected to the ground conductor layer via through holes formed in the dielectric substrate.

The microwave radiator element need not be limited to a coplanar microstrip configuration. In other examples it may comprise a travelling wave antenna, or meandering or interdigitated microstrip arrangement.

The opposing inner surfaces of the pair of jaws may include textured or ridged portions to retain biological tissue within the gap. This feature may also permit gas or vapour generated by the denaturing process at the sealing interface to escape.

The pair of jaws may be pivotable relative to each other about a hinge axis that lies transverse to a longitudinal axis of the coaxial transmission line. In one example, the pair of jaws comprises a static jaw that is fixed relative to the instrument shaft, and a movable jaw that is pivotably mounted relative to the static jaw to open and close the gap between the opposing inner surfaces. The energy delivery structure may be disposed on the inner surface of the static jaw. In another example, both jaws are arranged to pivot with respect to the instrument shaft, e.g. in a symmetrical forceps-type arrangement. Relative movement of the pair of jaws may be controlled from a handle at a proximal end of the instrument shaft. A control rod or control wires may pass through the instrument shaft to operably couple an actuation mechanism on the handle to the pair of jaws.

In another example, the pair of jaws may be arranged to move relative to one another in a manner that maintains the inner surfaces thereof in an aligned, e.g. parallel, orientation. This configuration may be desirable for maintaining a uniform pressure on grasped tissue along the length of the jaws. One example of such a closure mechanism is disclosed in WO 2015/097472.

In one example, the blade may be slidable in a longitudinal direction between a retracted position in which it lies proximal to the pair of jaws and an extended position in which it lies within the region between the pair of jaws. It is desirable for the blade to slide into the region between the blade when they are in a tissue gripping configuration, i.e. at least partially closed. The blade may be slidable along a longitudinally extending recessed groove formed in the pair of jaws, i.e. in each jaw of the pair of jaws, so that it can contact tissue held in the gap when the pair of jaws are closed. The groove may be arranged to act as a guide rail for the cutting blade, which may be particular useful where the pair of jaws curve towards their distal ends.

In another example, the blade may be mounted within one of the pair of jaws, and may be slidable or otherwise movable in a lateral direction between a retracted position in which it lies beneath the inner surface of the jaw and an extended position in which it lies within the region between the pair of jaws.

The blade may comprise a rigid element with a sharp edge adapted to slice biological tissue, e.g. a scalpel-type blade or the like. This type of blade is configured to perform a "cold" cut, which may be preferred because it carries a low risk of collateral thermal damage that is associated with other cutting techniques. However, the invention need not be limited to a cold cut blade. In other examples, the blade may comprise any one of: a bipolar radiofrequency cutting element, an ultrasound sonotrode, and a heatable wire element.

As mentioned above, the vessel sealer may advantageously provide auxiliary functions in addition to its primary microwave-based vessel sealing function. For example, the instrument shaft may be arranged to convey radiofrequency (RF) EM energy and the distal end assembly may be arranged to receive the RF EM energy from the instrument shaft. In this example, the distal end assembly may further comprise a dissector element arranged to deliver the RF EM energy for cutting through biological tissue, wherein the dissector element is located outside the region between the pair of jaws. Further details of the dissector element are disclosed below with reference to the second aspect, and are equally applicable here.

In a second aspect, the present invention provides a vessel sealer as discussed above with the dissector element but without the blade. According to the second aspect, there may thus be provided an electrosurgical vessel sealer comprising: an instrument shaft arranged to convey microwave electromagnetic (EM) energy and radiofrequency (RF) EM energy; a distal end assembly arranged at a distal end of the instrument shaft to receive the microwave EM energy and the RF EM energy from the instrument shaft, the distal end assembly comprising: a pair of jaws that are movable relative to each other to open and close a gap between opposing inner surfaces thereof; and a dissector element arranged to deliver the RF EM energy for cutting through biological tissue, wherein the pair of jaws comprise an energy delivery structure arranged to emit the microwave EM energy into the gap between the opposing inner surfaces, wherein the energy delivery structure is arranged to confine an emitted microwave field substantially within a region between the pair of jaws, and wherein the dissector element is located outside the region between the pair of jaws. Any features of the first aspect discussed above are equally applicable to the second aspect.

The dissector element may comprise a bipolar RF structure having an active electrode and a return electrode. The active electrode (cutting element) may be an order of magnitude smaller than the return electrode. The return electrode may be formed on an outer surface of the jaw adjacent to the dissector element, so that it is in direct contact with the tissue when used in a dry field. The dissector element may thus be used for small scale or fine cutting, e.g. to improve access to or open up a treatment site.

The cutting region may sit away from (i.e. proud) of the pair of jaws. For example, the dissector element may comprise a protruding body that presents a leading edge for contacting tissue. The active electrode may be provided at the leading edge, e.g. to ensure that the RF current density is concentrated in that region.

The dissector element may be mounted on an outer surface of the pair of jaws. For example, the protruding body may be on a distal or side surface of the pair of jaws. The protruding body may be formed from a suitable dielectric, with the active electrode being a conductive portion fabricated thereon. The return electrode may be on the protruding body or on the outer surface of the pair of jaws.

In another example, the dissector element may be mounted on a longitudinal extender, the longitudinal extender being movable longitudinally with respect to the pair of jaws. This arrangement can assist visibility of the dissector element in use, e.g. by enabling it to be moved into a treatment site before the pair of jaws.

In a preference example, the dissector element may be mounted at a distal end of the distal end assembly.

The microwave EM energy and RF EM energy may be conveyed along a common signal pathway through the instrument shaft. For example, a coaxial transmission line may provide the common signal pathway for conveying both the microwave EM energy and the RF EM energy. In this arrangement, the distal end assembly may comprise an inductive filter for blocking the microwave EM energy from the dissector element, and a capacitive filter for blocking the RF EM energy from the energy delivery structure on the pair of jaws. In an alternative arrangement, the RF EM energy and microwave EM energy are conveyed along separate pathways within the instrument shaft, wherein the inductive filter and capacitive filter are provided at a proximal end of the instrument shaft, e.g. in a handle.

As mentioned above, the distal end assembly and instrument shaft may be dimensioned to fit within an instrument channel of a surgical scoping device. The surgical scoping device may be a laparoscope or an endoscope. Surgical scoping devices are typically provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be equal to or less than 13 mm, preferably equal to or less than 10 mm, and more preferably, especially for flexible insertion tubes, equal to or less than 5 mm.

The vessel sealer discussed above may find applicability in other tissue welding techniques. For example, the energy delivery structure may be used as an alternative to staples. In some abdominal procedures, staple guns are used to deliver 50 to 100 small staples that are fired simultaneously between jaws that can have a length of 70 mm or more, or from an annular jawed arrangements with diameters of 20 to 50 mm. In this type of application multiple antenna structures such as those discussed herein may be used to cover the required length. The antenna structures may be arranged in any number of array forms to be activated simultaneously, sequentially or progressively in a suitable manner.

BRIEF DESCRIPTION OF THE DRAWINGS

Embodiments of the invention are described in detail below with reference to the accompanying drawings, in which:

FIGS. 6A and 6B show opposing surfaces of a first example coplanar microstrip antenna that can be used in an electrosurgical instrument that is an embodiment of the invention;

DETAILED DESCRIPTION; FURTHER OPTIONS AND PREFERENCES

Figure 1:
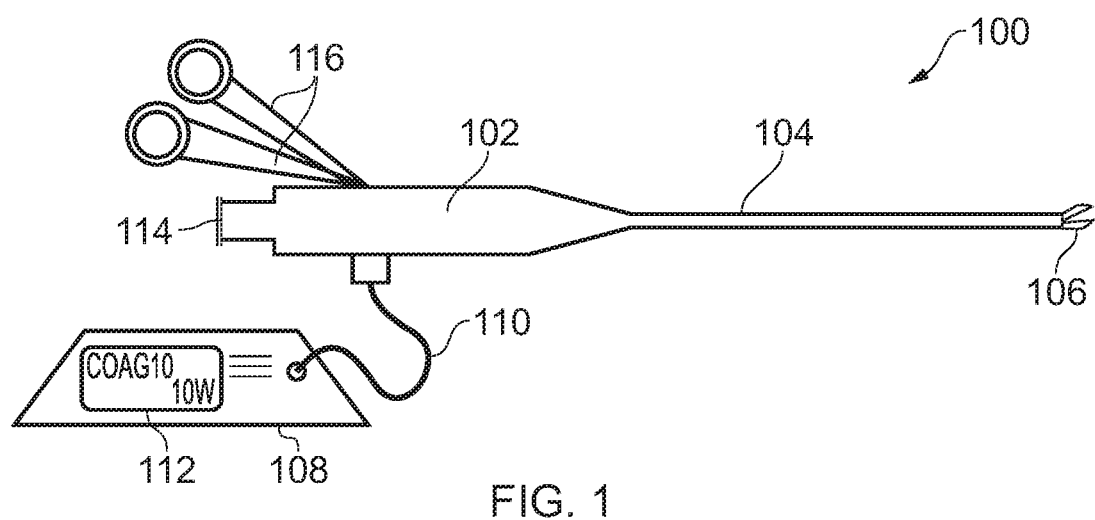
FIG. 1 shows a schematic view of an electrosurgical apparatus with which the present invention may be used.

The present invention relates to an electrosurgical vessel sealer device capable of delivering microwave energy to seal blood vessels. The device may be used in open surgery, but may find particular use in procedures where there is restricted access to the treatment site. For example, the electrosurgical vessel sealer of the invention may be adapted to fit within the instrument channel of a surgical scoping device i.e. laparoscope, endoscope, or the like. FIG. 1 shows a schematic view of an electrosurgery apparatus 100 in which the electrosurgical vessel sealer of the invention may be used.

The electrosurgery apparatus 100 comprises a surgical scoping device 102, such as a laparoscope. The surgical scoping device 102 has a rigid or steerable instrument shaft 104 suitable for insertion into a patient's body. The instrument shaft normally conveys at least two functional channels. One of the functional channels is an optical channel, which allows a distal treatment zone to be illuminated and imaged. Another functional channel is an instrument channel, which provides access for surgical instruments to the distal treatment zone. In this example, a distal tip assembly of a vessel sealer instrument 106 can be seen protruding from the distal tip from the instrument channel.

The electrosurgery apparatus may comprise an electrosurgical generator 108 capable of generating and controlling power to be delivered to the vessel sealer instrument 106, e.g. via power cable 110, which extends from the generator 108 through the surgical scoping device 102 and instrument channel to the distal tip. Such electrosurgical generators are known, e.g. as disclosed in WO 2012/076844. The electrosurgical generator 108 may have a user interface for selecting and/or controlling the power delivered to the instrument 106. The generator 108 may have a display 112 for showing the selected energy delivery mode. In some examples, the generator may allow for a energy delivery mode to be selected based on the size of the vessel to be sealed.

The surgical scoping device 102 may operate in a conventional manner. For example, it may comprise an eyepiece 114 or other optical system for providing an image of the distal tip, e.g. digital video imaging, to view the distal tip at point of application. Operation of the instrument 106 may be controlled by an actuation mechanism 116 (e.g. a scissor-type handle, slider, rotatable dial, level, trigger or the like). The actuation mechanism 116 can be operably coupled to the instrument 106 via one or more control wires that extend along the shaft 104, e.g. within the instrument channel.

In one example, the actuation mechanism may include a force limiter arranged to limit the maximum actuation force that can be supplied to the instrument. Limiting the maximum actuation force may assist in preventing damage to delicate components in the instrument 106, and can ensure that the force applied to tissue remains within desired parameters. The force limited may comprise a compression spring or ratchet mechanism as part of the actuation mechanism. In some examples it may be desirable to vary the maximum actuation force, e.g. by provide a dial or switch on the device 102 that adjusts the maximum actuation force associated with the actuation mechanism 116.

Embodiments of the present invention represent a development of the electrosurgical forceps disclosed in WO 2015/097472, and in particular relate to the structure and functionality of the distal tip assembly.

Figure 2:
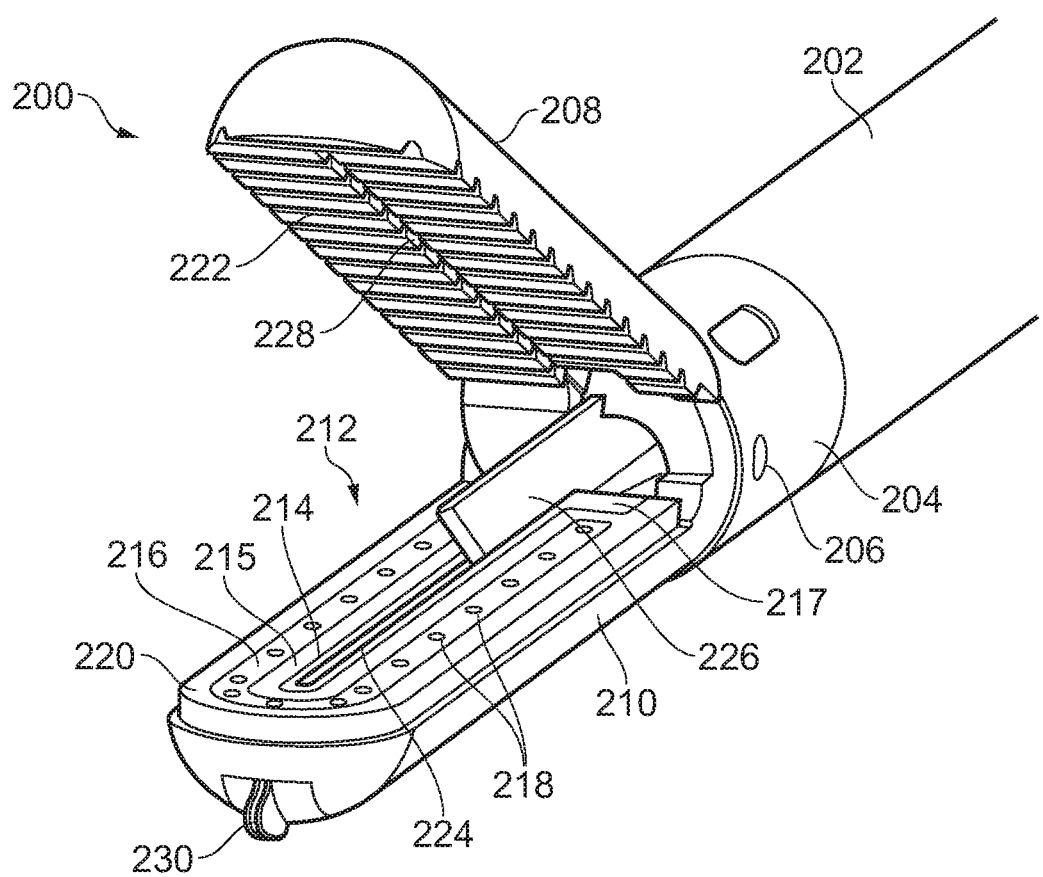
FIG. 2 shows a schematic perspective view of a distal tip assembly of an electrosurgical instrument that is an embodiment of the invention.

FIG. 2 shows a schematic perspective view of a distal end assembly 200 of an electrosurgical instrument that is an embodiment of the invention. The distal end assembly 200 is connected to an instrument shaft 202 which is dimensioned to fit within the instrument channel of a laparoscope or other surgical scoping device. The instrument shaft 202 comprises a tubular sheath that conveys a coaxial cable for carrying microwave power to the distal end assembly together with various control wires or rods that are arranged to control physical manipulation of the distal end assembly, as discussed below.

In this example, the distal end assembly 200 comprises a pair of jaws 208, 210. The jaws 208, 210 are operably coupled to a collar 204 that is mounted on a distal end of the instrument shaft 202. In this example, the pair of jaws 208, 210 comprise a movable jaw 208 which is pivotal around a laterally extending pin 206 in the collar 204 to enable a gap between opposing inner surfaces of the jaws 208, 210 to be opened and closed. Although there is only one movable jaw in this example, in other embodiments, both jaws may be arranged to pivot relative to the collar 204. The collar 204 may be arranged to ensure that the jaws remain laterally aligned as they are moved together.

The example shown in FIG. 2, the pair of jaws 208, 210 comprises a static jaw 210 that has an energy delivery structure 212 on its top surface, i.e. the surface that opposes a corresponding surface on the movable jaw 208. In use, the distal end assembly 208 is intended to grip biological tissues (and in particular a blood vessel) between the pair of jaws 208, 210. The pair of jaws 208, 210 are arranged to apply pressure to the biological tissue between the opposed surfaces and deliver energy (preferably microwave electromagnetic energy) into the tissue from the energy delivery structure 212.

In this embodiment, the energy delivery structure is present only on the static jaw 210. However, in other arrangements, there may be an energy delivery structure on both jaws, or only on a single movable jaw.

In this example, the energy delivery structure 212 comprises a coplanar microstrip antenna fabricated in the top surface of the status jaw 210. The coplanar microstrip antenna comprises a substrate 220 made of nonconductive dielectric material, e.g. ceramic or the like. The dielectric substrate 220 has a conductive layer fabricated on its underside (not visible in FIG. 2). On its top surface (i.e. the surface opposite the underside) the dielectric substrate 220 has a first conductive region in the form of a longitudinally extending finger electrode 214 disposed centrally thereon. A U-shaped second conductive region 216 is disposed on the top surface of the dielectric substrate 220 around the finger electrode 214 with a gap of exposed dielectric 215 separating the finger electrode 214 from the U-shaped region 216. A plurality of through holes 218 are formed, e.g. machined, through the U-shaped region 216 and dielectric substrate 215. The through holes 218 are filled with conductive material to electrically connect the conductive layer on the underside of the dielectric substrate 220 with the U-shaped conductive region 216. The finger electrode 214 has a contact pad 217 at a proximal end thereof. The inner conductor of the coaxial cable conveyed by the instrument shaft 202 is electrically coupled to the contact pad 217, e.g. by extending from the instrument shaft 202 to physically contact the contact pad 217. The finger electrode 214 provides an active region for the coplanar microstrip antenna. The conductive layer on the underside of the dielectric substrate 220 is electrically connected to an outer conductor of the coaxial cable conveyed by the instrument shaft 202. In conjunction with the conductive communication through the through holes 218, the U-shaped conductive region 210 forms a ground electrode for the coplanar microstrip antenna.

The configuration of the coplanar microstrip antenna shown in FIG. 2 is particularly advantageous because it confines the emitted field within the region defined by the pair of jaws 208, 210. As discussed below, very little energy is delivered to a region outside the pair of opposing surfaces. Moreover, by arranging the U-shaped conductive region 216 to extend around a distal end of the finger electrode 214, the coplanar microstrip antenna structure can prevent energy from escaping in the longitudinal direction distal to assembly 200.

The conductive layers mentioned above may be made from any suitable conductive material. Silver and gold are preferred because of their high conductivity and biocompatibility. Copper may also be used, although it is preferably plated with silver or gold in regions likely to contact biological tissue.

The coplanar microstrip antenna structure may be fabricated independently of the static jaw 210, e.g. using thin film deposition techniques. This construction of the coplanar microstrip antenna ensures two important performance features. Firstly, it ensures that the projected energy applied to the biological tissue of the gripped vessel is focused inwardly within the grasp of the instrument jaws. This provides a localised energy delivery effect, whereby the applied energy is efficiently delivered to a desired region of tissue.

Moreover, the use of thin film conductive layers means that the thermal mass of the conductive lines is minimal. In combination with the effective thermal barrier provided by the dielectric substrate 220, this means that any residual heat within the conductive lines quickly dissipates. The effect can be further enhanced by providing a layer on the surface opposing the coplanar microstrip antenna that also acts as a thermal barrier. In the embodiments shown in FIG. 2, the moveable jaw 208 has a layer of resiliently deformable material 222 formed on its inner surface. The layer 222 may be formed from silicone rubber or other compliant polymer material that can withstand the temperatures that occur during treatment and are biocompatible. They may be fabricated from an elastomeric thermoplastic polymer, for example. This layer both assists in efficient delivery of energy to gripped biological tissue, but also facilitates retaining the biological tissue within the jaws.

Alternatively of additionally, a coating may be applied to the surface of the coplanar microstrip antenna itself. This may be a coating applied only to the conductive regions, e.g. to minimise tissue sticking. In embodiments arranged to deliver microwave energy, it may not be necessary for the inner surfaces of the jaws to may direct electrical conductive contact with tissue. Accordingly, the coating may be a thin high temperature polymeric material, e.g. applied across the whole face of the antenna. The specific material may be chosen to exhibit high loss and appear transparent to the microwave energy.

The coating may conform to the shape of the jaws. It may comprise a silicone-based passivation material similar to that used as a protective coating on printed circuit boards. Other examples include polyimide, PTFE or FEP type materials.

As shown in FIG. 2, the layer 222 has a plurality of ridges moulded into it. It therefore presents a textured or toothed surface with which to contact biological tissue. A similar ridged or textured grip may be provided around the periphery of the coplanar microstrip antenna. As mentioned above, these textured surfaces can aid the release of gas during the vessel sealing operation.

The coplanar microstrip antenna has a size suitable for receiving and sealing biological vessels. For example, the coplanar microstrip antenna may be arranged to provide an effective treatment area having a width (i.e. dimension extending laterally with respect to the axis of the coaxial cable) of 2 to 5 mm and a length (along the axis of the device) of 15 to 26 mm.

The pair of jaws may include a stand off (not shown) that ensures that the jaws remain separated by a minimum distance irrespective of the closure force applied by the actuation mechanism 116. The stand off may be a physical projection on one or both jaws that engages the inner surface of the opposite jaw.

It is desirable for the pressure applied by jaws to tissue held therebetween to be uniform in a longitudinal direction along the inner surfaces of the jaws. In a development of the structure shown in FIG. 2, the movable jaw 208 may comprise an engagement plate at its inner surface that is capable of articulating back into the jaw 208 about a pivot point located at a distal end of the jaw 208. A resiliently deformable support element may be mounted in the jaw 208 behind the engagement plate to urge it outwardly. With this arrangement, tissue in the region between the jaws is grasped between the inner surface of the static jaw and the engagement plate of the movable jaw. As the jaws are closed, the pressure applied along the jaws is generated by a combination of the pivoting action of the jaws and the articulation of the engagement plate. The location of the pivot point and properties of the resiliently deformable support element can be selected so that the non-uniformity in applied force that arises changing mechanical advantage along the jaws away from the pivot is balanced by a cooperating non-uniformity arising from the pivotable articulation of the engagement plate.

The energy delivery structure 212 described with respect to FIG. 2 is a coplanar microstrip antenna. The configuration of that antenna may be as shown in FIG. 2 or as described with reference to any of FIGS. 6A, 6B, 7A, 7B, 8A and 8B below. However, alterative microwave radiator structures can be used. For example the top surface of the static jaw 210 may be provided with other microstrip-based energy delivery configurations, e.g. meandering or interdigitated microstrip lines. In another embodiment, the energy delivery structure may be a travelling wave antenna, such as that described with reference to FIG. 11 below.

In addition to the function of the vessel sealing, the electrosurgical instrument of the present invention may also function as a vessel divider, e.g. to cut through and separate a sealed section of a blood vessel. The vessel sealer may therefore be provided with a blade 226 that is slidably mounted with respect to the pair of jaws 208, 210 to cut through biological tissue held between the jaws.

In FIG. 2, the blade 226 is a sharp scalpel-type structure, made of steel or other hard material. For clarity, the blade is shown as protruding into the region between the open jaws in FIG. 2. However, in practice, it is desirable for the instrument to prevent forward movement of the blade until after the jaws are closed and microwave energy is applied.

In the embodiment shown in FIG. 2, the blade 226 is movable in a longitudinal direction, e.g. along the axis of the device. The opposed surfaces of the jaws 208, 210 contain respective recess or guide grooves 228, 224 for receiving the blade as it travels. The guide groove 224 in the static jaw 210 is formed within the finger electrode 214 so that is moves through the centre of the applied field.

In other embodiments, the blade may be mounted within one of the jaws and arranged to move laterally with respect to the longitudinal direction, i.e. to extend out of one of the opposed surfaces into gripped tissue. The sharp edge of the blade may lie below the opposed surface during the vessel gripping and sealing operation.

It is preferred for the blade to provide a "cold" cut, as this functionality is associated with better patient outcomes. This is primarily because the risk or occurrence of collateral damage, i.e. thermal damage to surrounding tissue is much less when cold cutting is used. However, cutting functionality can be provided by other means, e.g. a radiofrequency (RF) monopolar or bipolar energy delivery structure, or an ultrasonic cutting mechanism. An arrangement for delivering auxiliary power down the instrument shaft, e.g. for either an RF cutting blade or an ultrasonic system, is discussed below.

The distal end assembly may be configured to perform functions in addition to vessel sealing. For example, the distal end assembly may have an auxiliary radiofrequency (RF) cutting blade mounted on a distal tip thereon. In the example shown in FIG. 2, an RF dissector element 230 is mounted on the distal end of the static jaw 210. The RF dissector element 230 is a bipolar structure that comprises an active electrode mounted on a protruding body, and a return electrode, which may be fabricated on or integrated with the static jaw 210 in the vicinity of the protruding body.

Figure 3:
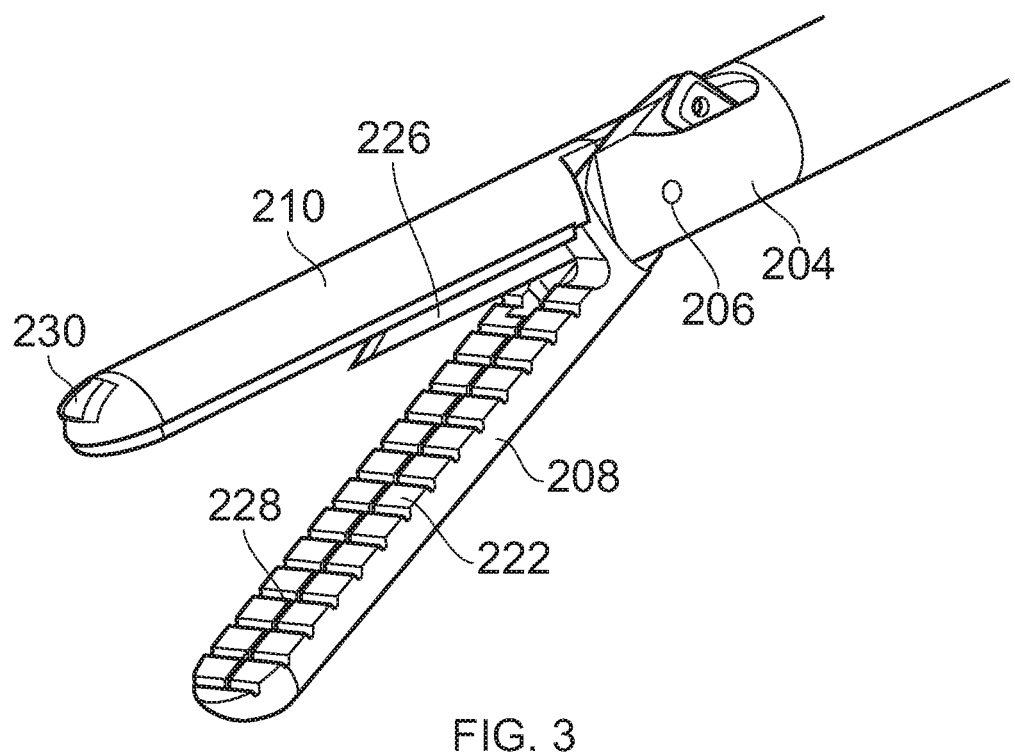
FIG. 3 shows a schematic perspective view of the underside of the distal tip assembly shown in FIG. 2.
Figure 4:
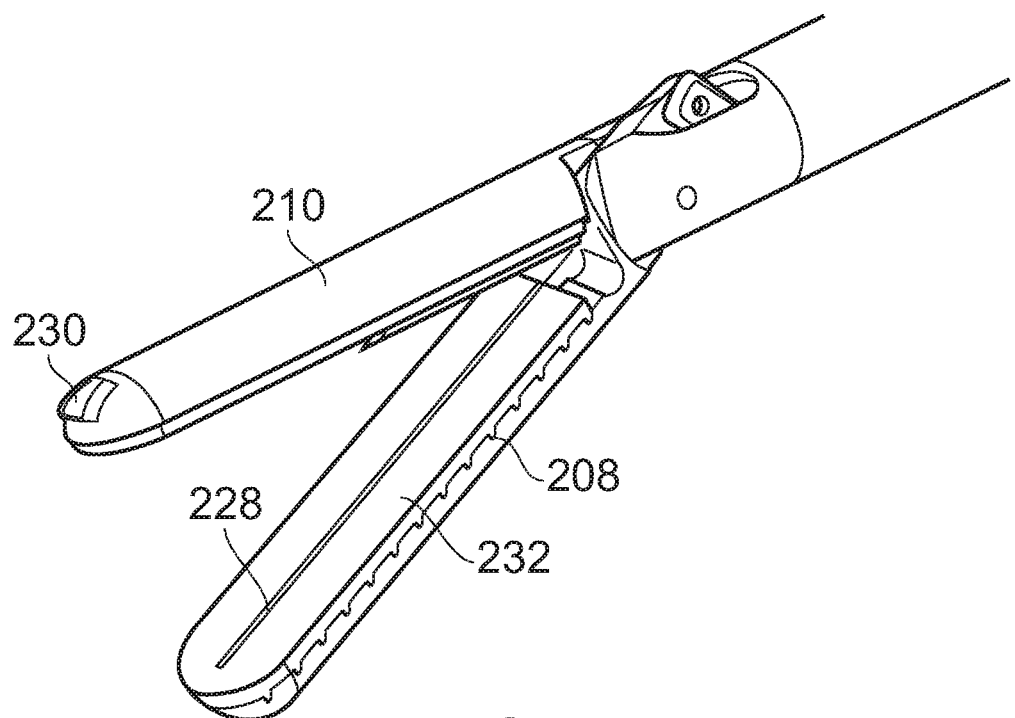
FIG. 4 shows a schematic perspective view of an underside of a distal tip assembly of an electrosurgical instrument that is another embodiment of the invention.

FIG. 3 shows the underside of the distal end assembly 200, where the RF dissector element 230 can be seen in more detail. The RF dissector element 230 can be used for fine bloodless tissue cutting and tissue dissection. In the arrangement shown in FIGS. 2 and 3, the RF dissector element 230 presents a leading edge that sits proud of the distal end of the static jaw 210 This position can enable both side and end-on dissection to be performed. In dry field treatment scenarios (i.e. in the absence of saline or other electrically conductive fluid) it is desirable for the return electrode to be in close proximity to the active electrode that is on the RF dissector element 230. The ratio of the exposed tissue contacting electrode areas is also important to ensure that current flow occurs in a desired manner that causes maximum current density to occur on the leading edge of the RF dissector element 230.

Although the RF dissector element 230 is shown at the distal end of the static jaw in FIGS. 2 and 3, it can be mounted in a variety of orientations or locations on the distal end assembly, e.g. vertically, horizontally, at an angle, on one side, and on either jaw.

The distal tip assembly may comprise other energy delivery elements mounted on one of the jaws to enable fine treatment work to be done at the distal end of the device. For example, the jaw may include a small microwave antenna for enabling fine microwave coagulation, or a small ultrasonic sonotrode for delivering ultrasonic energy to perform cutting. These auxiliary elements may be mounted on an independently slidable member that can be longitudinally extended and retracted with respect to the instrument shaft 202. This can assist in improving visibility of fine treatment using the auxiliary device, as it can be extended into the field of view of the surgical scoping device independently of the rest of the distal end assembly 200. In one embodiment, the independently slidable member may be the static jaw 210, which can be dislocated from the collar 204 to enable it to slide longitudinally. The static jaw may be either retractable proximally away from its normal hinged location, or may be extendable distally away from its normal hinged location. In the latter scenario, the RF fine dissection tip or other auxiliary function may be located on the static jaw, so that it is can be moved into a distalmost position. In the former scenario, the RF fine dissection tip or other auxiliary function may be located on the opposing jaw so that is occupies a distalmost position having good visibility when the static jaw is retracted.

The pair of jaws may have any suitable shape. For example, the jaws may be tapered along their length towards the distal tip, or may be bent or hooked if desired for any particular treatment scenario.

Opening and closing of the jaws 208, 210 may be controlled by an actuation mechanism that is operable by a user at an external handle of the surgical scoping device, i.e. at a proximal end of the instrument shaft 202. The actuation mechanism may include a pressure control device arranged to enable a user to control closure of the pair of jaws based on an amount of pressure applied to the biological tissue that is captured between the jaws. In one example, a user may select a desired (e.g. maximum) closure pressure for the jaws, and the actuation mechanism may be arranged to inhibit further movement of the jaws towards each other once the desired pressure is reached.

As mentioned above, in some embodiments, both of the jaws may be active in the sense that they are electrically connected to a coaxial cable within the instrument shaft. In one example the pair of jaws comprise different elements of a single microwave energy delivery device. For example, one of the jaws may comprise a ground electrode, and the other may comprise an active electrode for an antenna structure. In another example, each jaw may comprise its own independent microwave energy delivery structure, e.g. corresponding to the coplanar microstrip antenna described above.

If both of the jaws are active, they may be fed from a common coaxial transmission line within the instrument shaft by providing a microwave power divider or splitter at the distal end of the coaxial transmission line, e.g. at the distal end of the instrument shaft, or within the collar 204. The microwave power splitter may be implemented in any known manner. For example, the power splitter could be implemented as a Wilkinson power splitter, as two quarter wavelength (or odd multiple thereof) impedance transformers or as a half wavelength balun arrangement, where the distal end of the coaxial line forms an unbalanced feed that is input to the first jaw, and where the second jaw is fed from a point that is half an electrical wavelength away from the feed. Alternatively, the power splitter may be implemented as half electrical wavelength impedance transformers that are fabricated using flexible substrate materials, which are able to flex to allow for moving one or both jaws.

In arrangements where the distal end assembly also includes an auxiliary device for delivering RF energy, the instrument may be arranged to receive the RF energy for the auxiliary device and the microwave energy for delivery from the jaws along a common energy delivery pathway, which may be a coaxial transmission line within the instrument shaft. In one example, RF energy may be delivered at 400 kHz, whereas the microwave energy may be delivered at 5.8 GHz. In order to prevent the microwave energy from entering the auxiliary device an inductive blocking or filtering component may be mounted within the distal end assembly. The inductive block may be a wire-wound inductor, which permits RF energy to pass through the use of parasitic effects, but blocks microwave energy. Alternatively, the inductive block may be provided by one or more quarter wavelength open stubs located at half wavelength intervals along a transmission line between the coaxial cable and the auxiliary RF device. In order to prevent RF energy from entering the microwave energy delivery structure in the jaws, a capacitive block or filter element may be mounted between the coaxial cable and the microwave energy delivery structure. The capacitive filter element may be a parallel plate capacitor that operates at microwave frequencies, or a waveguide cavity or coupled microstrip line where an insulating dielectric breaks the conductive path in the manner that blocks flow of RF energy.

Similar blocks or filters may be used at the generator to prevent RF energy from entering the microwave source and microwave energy from entering the RF source. For example one or more chokes may be provided to prevent microwave energy from radiating into the RF source.

In the example above, the RF and microwave energy is carried along the instrument shaft by a common coaxial transmission line. In other examples, the separation of the RF and microwave energy may occur before they are delivered into the instrument shaft. In this arrangement, separate energy conveying structures are provided for the RF energy and microwave energy respectively. For example, the RF energy can be conveyed by a twisted wire pair or two insulated wire assemblies mounted in parallel, whilst the microwave energy is carried by a suitable coaxial transmission line. Power, e.g. DC power, for other types of auxiliary device, e.g. ultrasound blades or the like, can be delivered in a similar manner.

Initial histology analysis of samples treated using the vessel sealer discussed above show very promising outcomes, especially when compared to histological results of other forms of electrosurgical or ultrasonic vessel sealers. In particular, the microwave energy delivery configuration discussed above provides localised and controllable energy delivery that manifests itself as even cellular disruption within the sample, which leads to a well-defined seal location and, importantly, very limited propagation of heat beyond the seal. In other words, the thermal margin of the device, i.e. the amount of tissue blanching that occurs outside the gripped region, is small. The field shape and power loss density associated with the coplanar microstrip antenna is discussed in more detail below.

Figure 5:
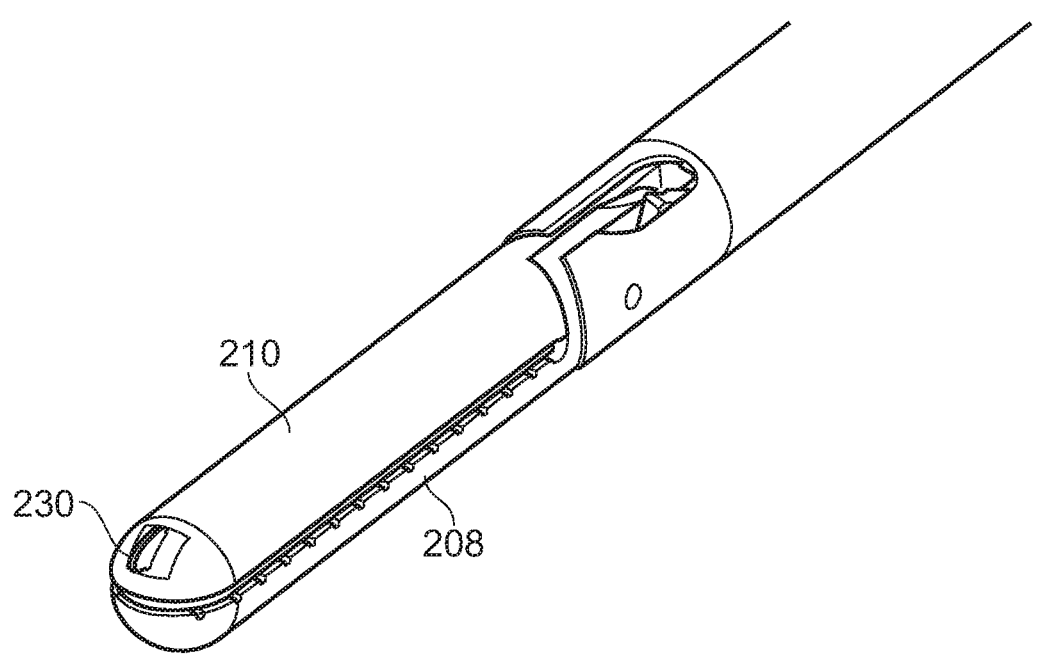
FIG. 5 shows a perspective view of the underside of the distal tip assembly shown in FIG. 2 in a closed configuration.

FIG. 5 shows a view of the underside of the distal end assembly when the jaws 208, 210 are closed. This is a configuration in which the instrument may be introduced to an instrument channel of a laparoscope.

FIGS. 6A and 6B show in more detail a first example of a coplanar microstrip antenna that can be used as an energy delivery structure 212 in an embodiment of the invention. The coplanar microstrip antenna comprises a dielectric substrate 220 which has a conductive ground layer 236 on its under surface (see FIG. 6B) and a pair of conductor lines 214, 216 on its upper surface. The ground layer 236 and the conductor lines 214, 216 may be formed on the substrate using any suitable technique, e.g. metallisation, thin film deposition and patterning (etching), etc.

As discussed above, the pair of conductive lines 214, 216 in this example comprise a finger electrode 214 that is surrounded along its length and around its distal end by a U-shaped conductive region 216. The U-shaped conductive region 216 is electrically connected to the ground layer 236 via through holes 218, 238 which are filled with conductive material to provide an electrical connection. The finger electrode 214 and u-shaped conductive region 216 are separated by a gap 215 across which the microwave field is concentrated in use. The ground conductor 236 is in electrical communication with an outer conductor of a coaxial feedline, whereas the finger electrode 214 is electrically connected to an inner conductor of the coaxial feedline.

Figure 7A:
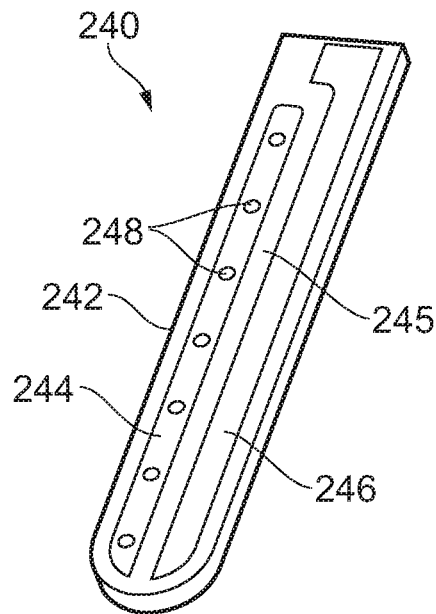
FIGS. 7A and 7B show opposing surfaces of a second example coplanar microstrip antenna that can be used in an electrosurgical instrument that is an embodiment of the invention.
Figure 7B:
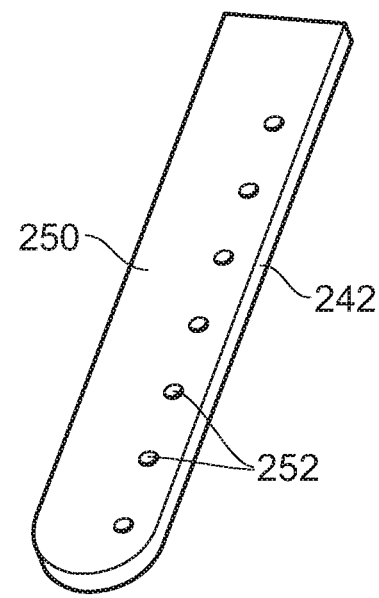

FIGS. 7A and 7B show a second example of a coplanar microstrip antenna 240 that can be used in the present example. Similar to the example shown in FIGS. 6A and 6B, the antenna 240 comprises a dielectric substrate 242 having an underside that has a conductive layer 250 thereon, e.g. metallised or otherwise applied. The top surface of the dielectric substrate 242 (shown in FIG. 7A) comprises a pair of elongate conductive element which extend parallel with one another in the longitudinal direction of the jaw in which the antenna will be mounted. The conductive elements comprise a ground conductor finger 244 and an active conductor 246, which are separated by a gap 245. The ground conductor finger 244 is in electrical communication with the ground conductor layer 250 via through holes 248, 252 that are machined through the dielectric substrate 242 and filled with conductive material to provide the necessary connection. Similarly to the arrangement shown in FIGS. 6A and 6B, the ground conductor layer 250 is to be electrically connected to an outer conductor and feed coaxial feed line, whereas the active conductor finger 246 is to be electrically connected to an inner conductor of the coaxial feedline.

Figure 8A:
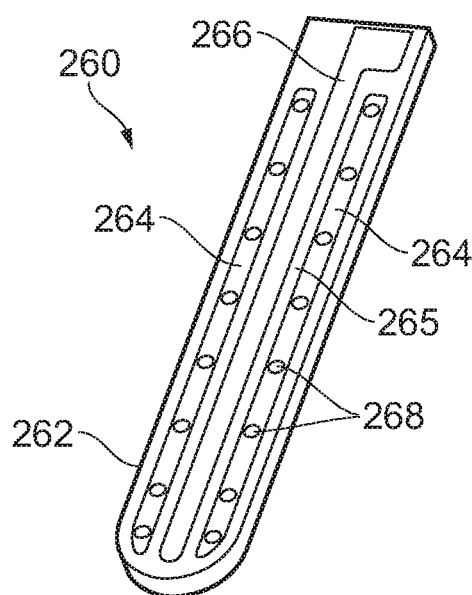
FIGS. 8A and 8B show opposing surfaces of a third example coplanar microstrip antenna that can be used in an electrosurgical instrument that is an embodiment of the invention.
Figure 8B:
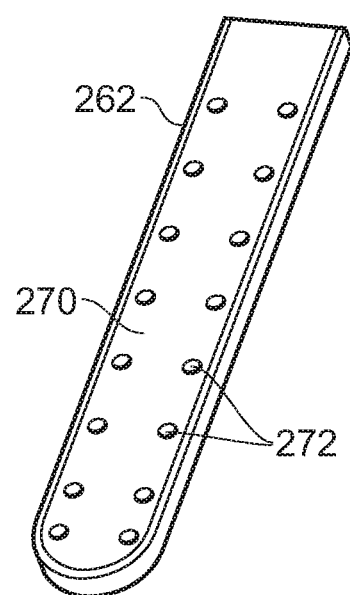

FIGS. 8A and 8B show a third example of a coplanar microstrip antenna 260 that can be used in the invention. The coplanar microstrip antenna comprises a dielectric substrate 262 having a ground conductor layer 270 on an underside thereof. On an upper surface of the dielectric substrate 262, there are three conductive elements. In this embodiment, the conductive elements comprise a central active finger electrode 266 on each side by a ground conductor strip 264. The ground conductor strips 264 and the finger electrodes 266 are elongate elements that extend in the longitudinal direction of the device. The active finger electrode 266 is separated from each of the ground conductor strips 264 by a gap 265 across which the microwave field extends in use. The ground conductor strips 264 are electrically connected to the ground conductor layer 270 via a plurality of through holes 268, 272, which are filled with conductive material to provide the necessary connection.

In the examples given above, the electrodes on the top surface of the dielectric substrate will contact tissue in use, and therefore are made from a biocompatible conductive material, such as silver or gold. In contrast, the ground conductor layer on the underside of the dielectric substrate does not contact tissue, and therefore may be made from a different material, such as copper.

Figure 9:
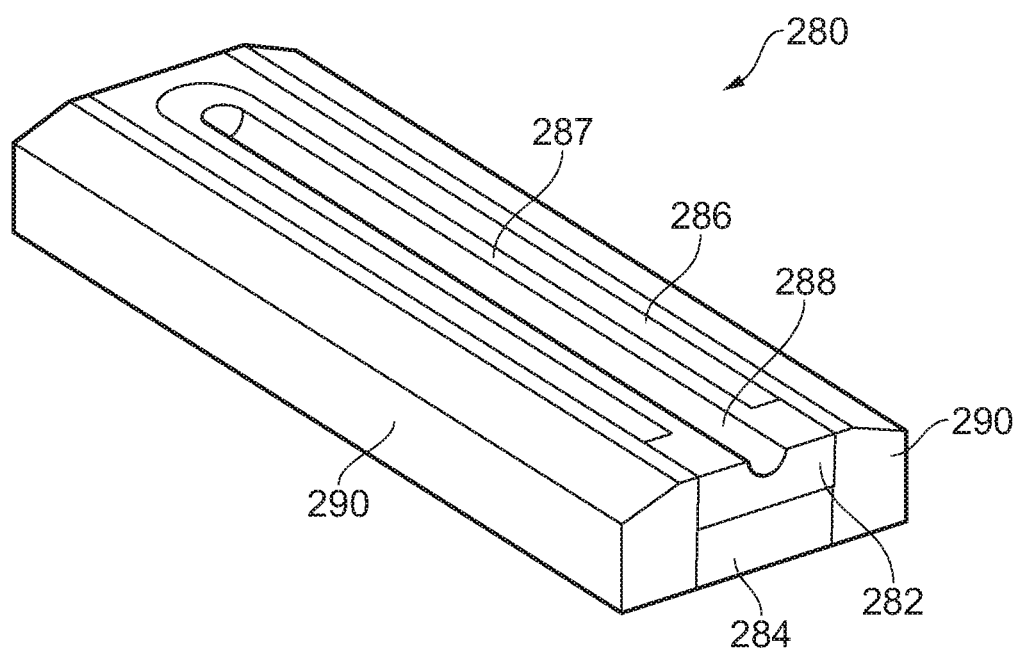
FIG. 9 shows a first example of an antenna blank suitable for connecting to a coaxial feed.

FIG. 9 shows another example of a coplanar microstrip antenna that can be used in the present invention. In this case, the antenna structure may be fabricated by machining one or more blocks of dielectric material. The structure shown in FIG. 9 is an antenna blank arranged to be mounted directly to a coaxial cable. The antenna blank 280 comprises a central dielectric block 282 that has a ground conductor layer 284 fabricated on its underside and a U-shaped conductive region 286 fabricated on its upper surface. The ground conductive layer 284 is electrically connected to the U-shaped conductive region 286. The dielectric block 282 is flanked by two side dielectric blocks 290 which assist in mounting the blank within a jaw structure and provide isolation for the ground conductor layer 284. A groove 288 is fabricated into the top surface of the dielectric block 282 in order to receive an exposed portion of an inner conductor of a coaxial feed line (not shown). The groove is separated from the U-shaped conductive region 286 by a gap 287. The antenna is formed by mounting a coaxial feedline with an exposed section of inner conductor on the proximal end face of the antenna blank 280. The exposed length of any conductor lies in the groove 288, and the ground conductive layer 284 is electrically connected to the outer conductor of the coaxial feedline.

Figure 10:
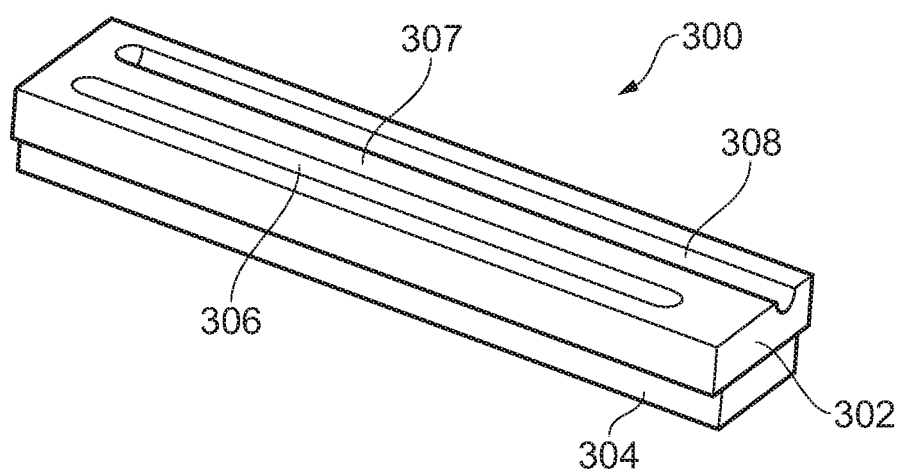
FIG. 10 shows a second example antenna blank suitable for coupling to a coaxial feed.

FIG. 10 shows another example of an antenna blank 300 that can be used in conjunction with a coaxial feed line to form a coplanar microstrip antenna that can be used in the invention. The antenna blank 300 comprises a dielectric substrate 302 that has a ground conductor layer 304 on its under surface. On the top surface of the dielectric substrate 302 there is an elongate ground conductor strip 306 that is electrically connected to the ground conductor layer 304, e.g. through the body of the dielectric substrate 302. Lying alongside and parallel to the ground conductor strip 306 is a groove 308 for receiving an exposed inner conductor of a coaxial feed. The ground conductor strip 306 and the groove 308 are separated by a gap 307 across which the microwave EM fields propagate in use. Similarly to FIG. 9, the antenna blank 300 can be used to form a coplanar microstrip antenna by connecting it to a coaxial feed that has a length of exposed inner conductor. The exposed inner conductor is received in the groove 308, while the outer conductor of the coaxial feed is electrically connected to the ground conductor layer 304.

Figure 11:
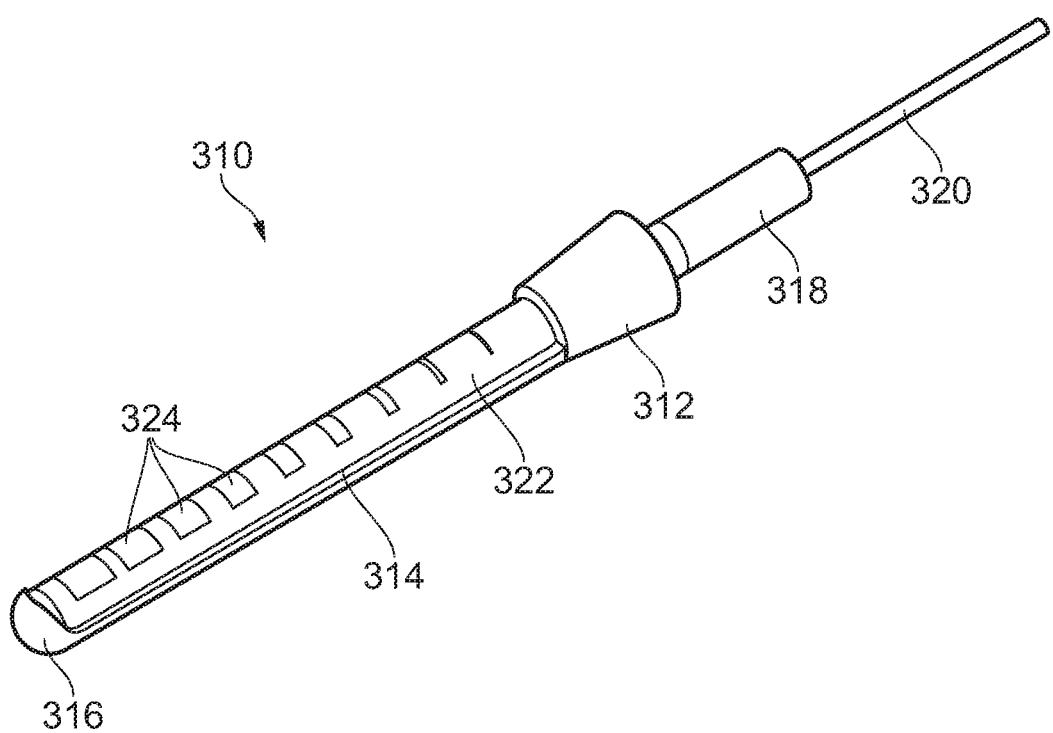
FIG. 11 is a schematic perspective view of a cylindrical travelling wave energy delivery structure that can be used in an electrosurgical instrument that is another embodiment of the invention.

The discussion above provides a number of examples of how a coplanar microstrip antenna can be used as the microwave energy delivery mechanism for the present invention. However, other microwave energy delivery structures can be used. FIG. 11 illustrates an example of a travelling wave antenna structure 310 that can be mounted within a jaw of a vessel sealer according to an embodiment of the invention. The travelling wave structure 310 comprises a housing for retaining a distal length of a coaxial cable. The housing comprises a proximal collar 312 through which the coaxial cable can be inserted, an elongate support base 314, and a distal cap 316, which acts as an end stop for a distal end of the coaxial cable. The antenna structure itself comprises an inner conductor 320 surrounded by a dielectric material 318 and an outer conductor 322. Within the outer conductor 322 a plurality of windows 324 are formed to expose the dielectric material. The windows may be formed within the outer conductor of the coaxial cable itself, or a separate conductive ground tube can be provided within the housing, and a coaxial cable having a distal end portion in which the outer conductor has been removed can be inserted therein. In FIG. 11, the outer conductor 322 comprises a deep drawn tube having closed distal end. The windows are slots cut into the tube before it is mounted on the dielectric material 318. The housing 312 and cap 316 may be fabricated in one piece and form a reinforcing member that supports the antenna by holding it straight and rigid.

The shape and position of the windows 324 on the outer conductor 322 are positioned to promote energy to be emitted. The size of the windows are varied along the length of the device so that energy is delivered in a directional manner normal to the longitudinal axis and uniformly along the length of the antenna.

Figure 12A:
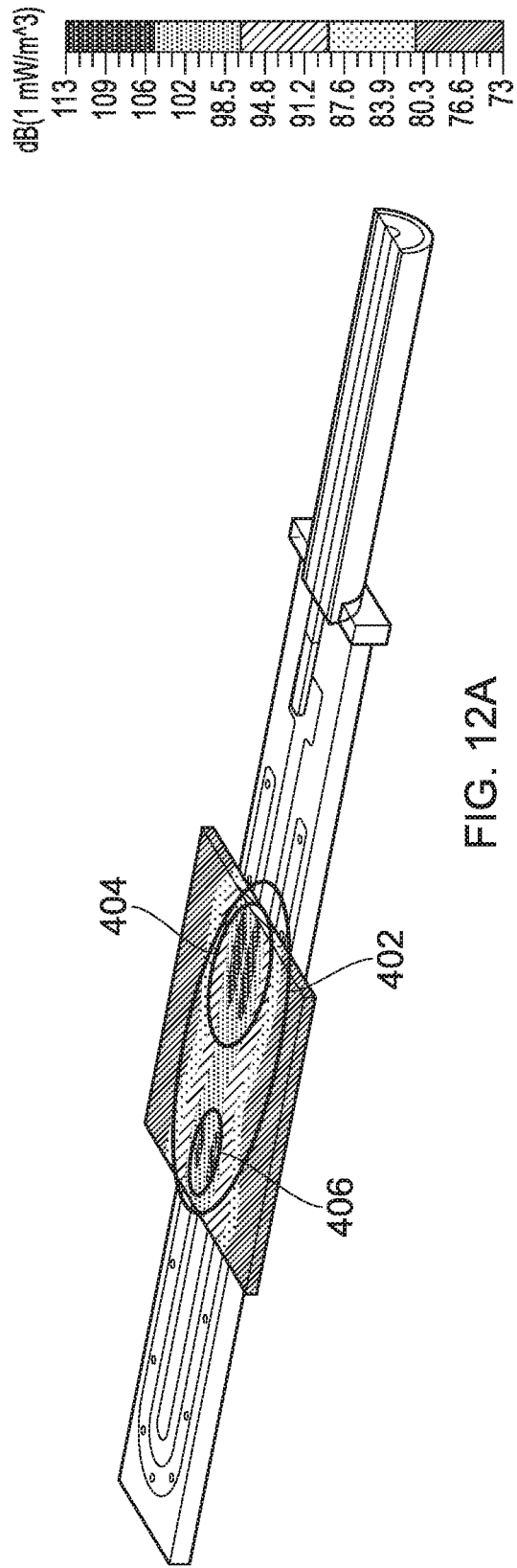
FIGS. 12A and 12B are simulated power loss density plots showing how microwave energy is delivered into biological tissue by a first example of a coplanar microstrip antenna.
Figure 12B:
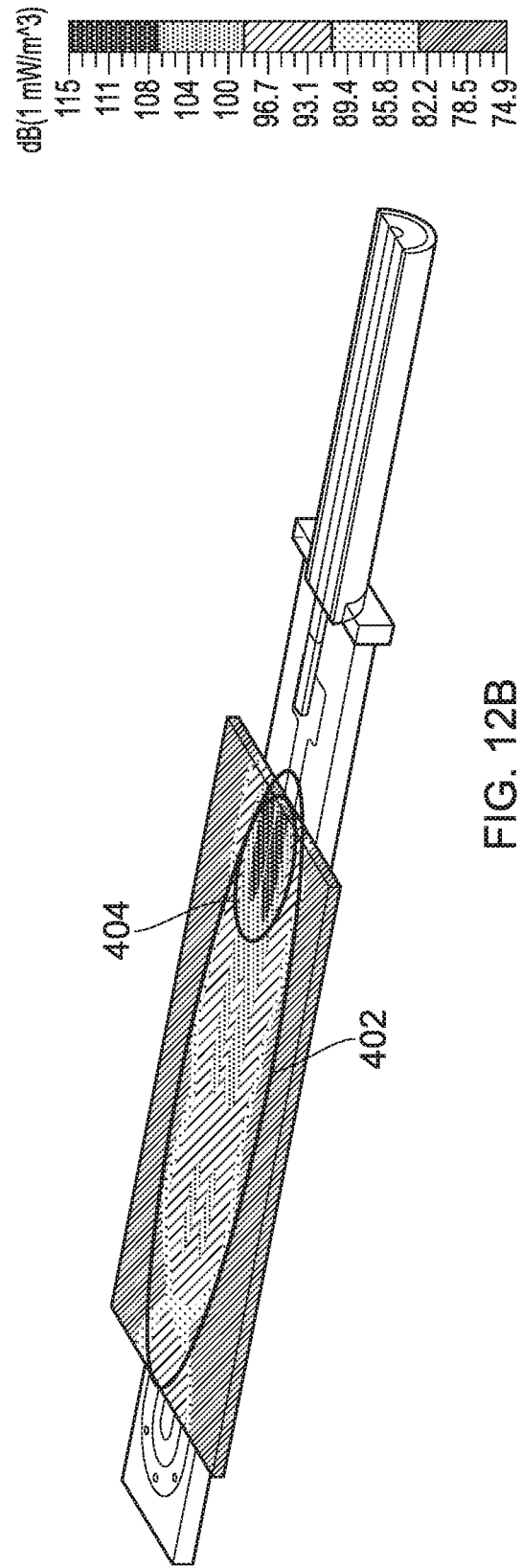
Figure 13A:
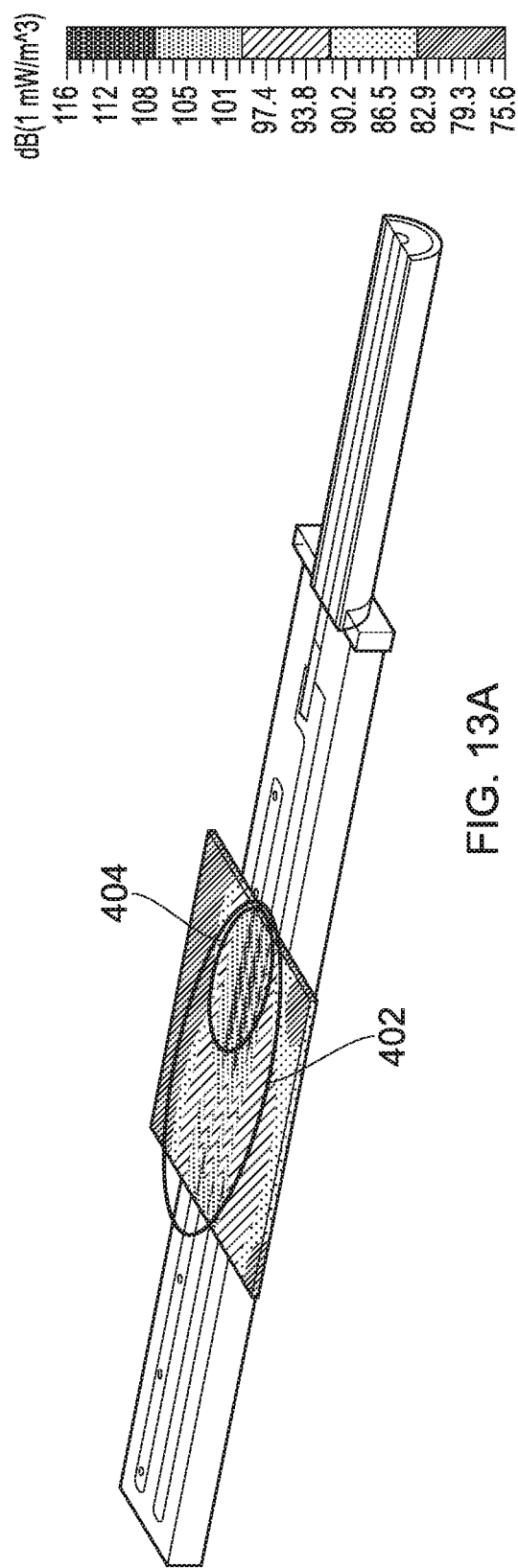
FIGS. 13A and 13B are simulated power loss density plots showing how microwave energy is delivered into biological tissue by a second example of a coplanar microstrip antenna.
Figure 13B:
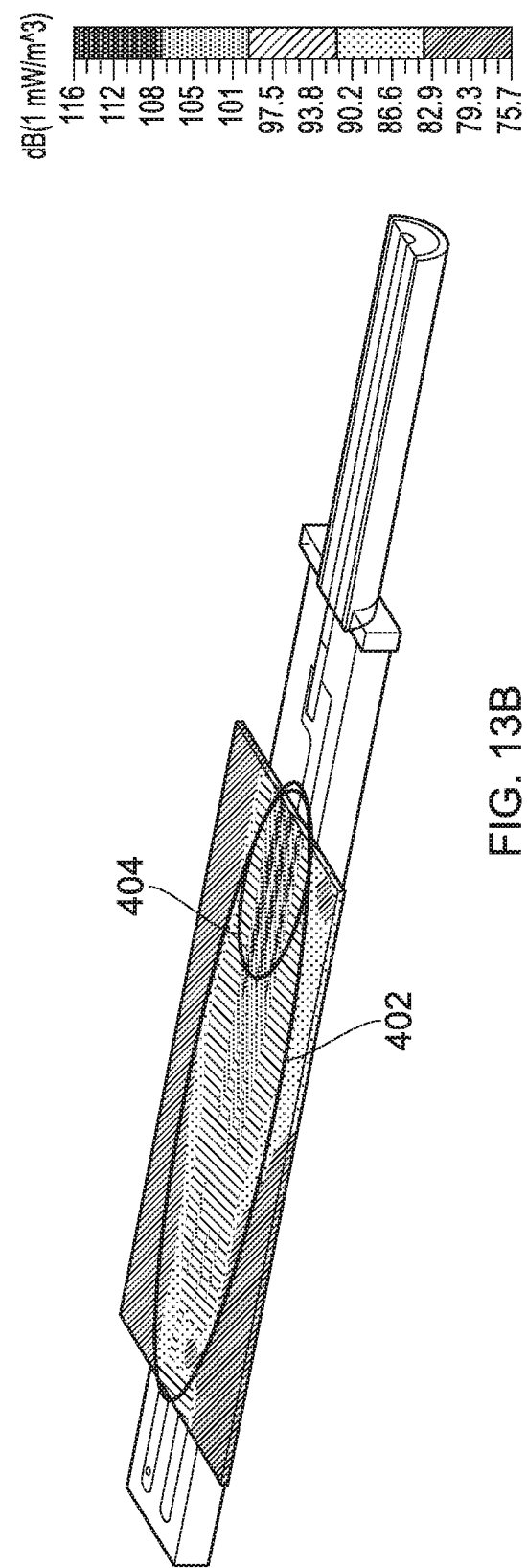
Figure 14A:
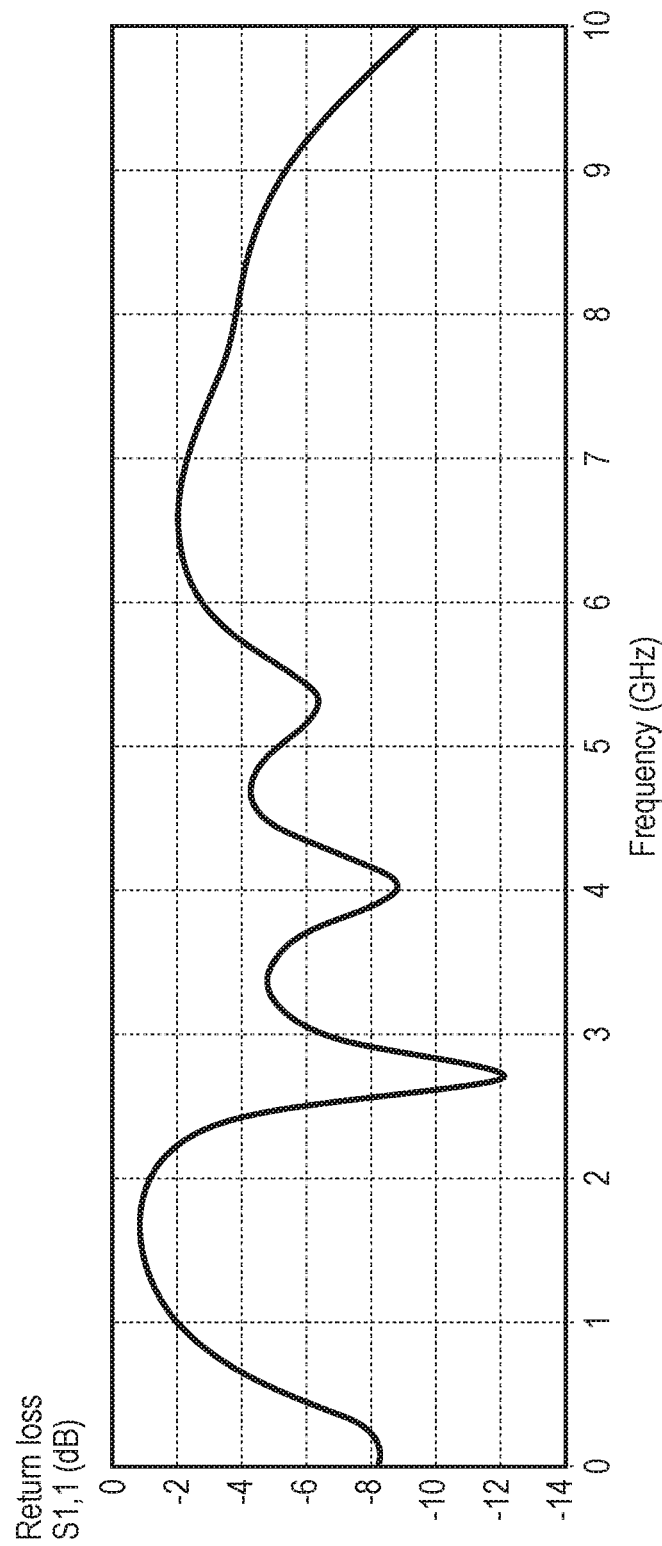
FIGS. 14A and 14B are simulated return loss plots for the arrangement shown in FIGS. 12A and 12B respectively.
Figure 14B:
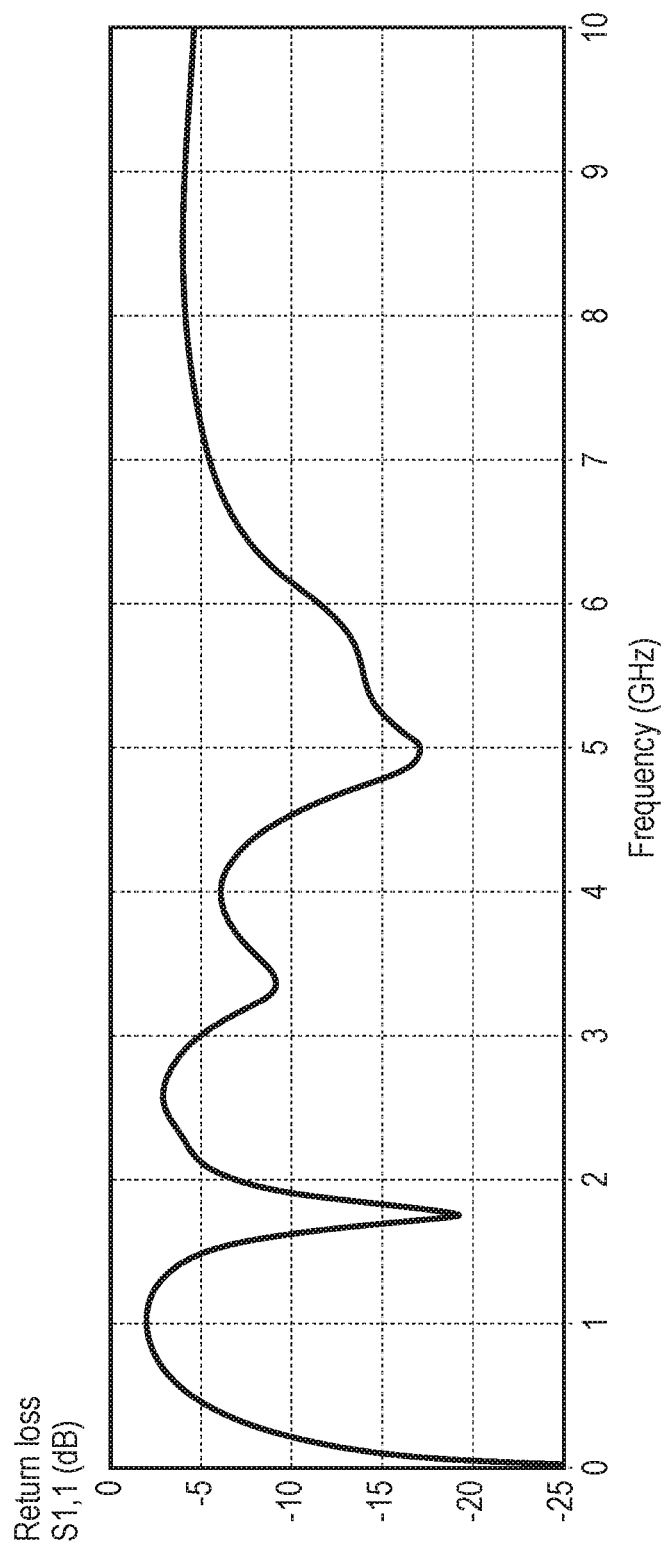
Figure 15A:
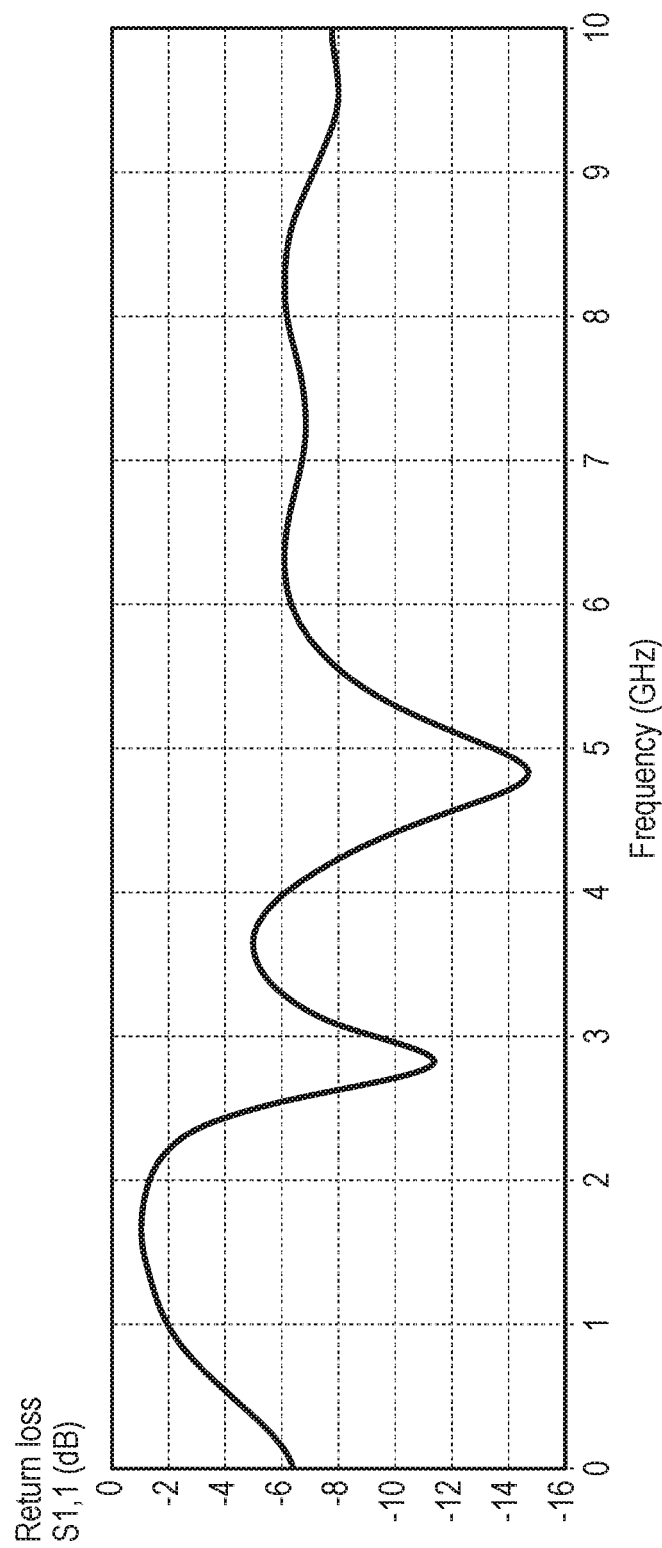
FIGS. 15A and 15B are simulated return loss plots for the arrangement shown in FIGS. 13A and 13B respectively.
Figure 15B:
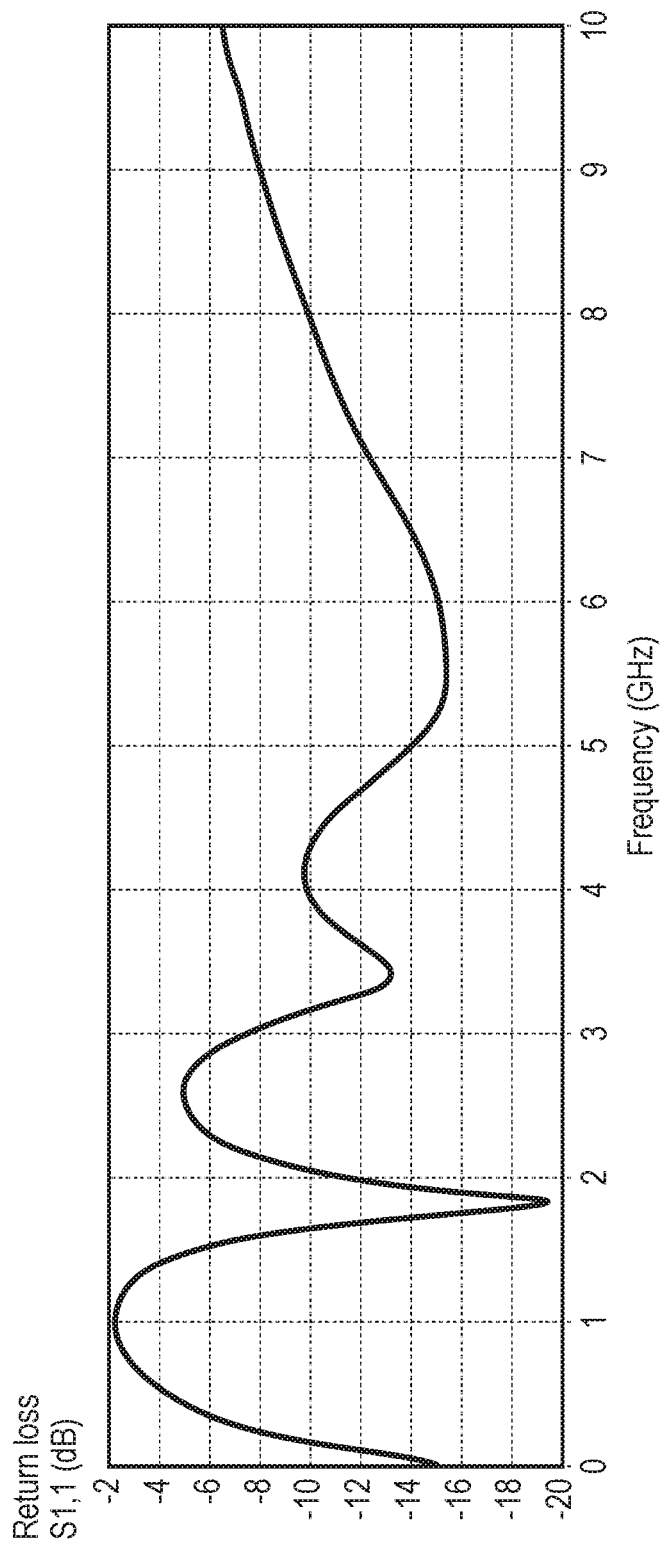

FIGS. 12A and 12B each show a simulated power loss density plot that demonstrates how microwave energy is delivered into biological tissue by a first example of a coplanar microstrip antenna. FIGS. 13A and 13B show the same information for a second example of a coplanar microstrip antenna. Each plot simulates a blood vessel clamped onto a jaw surface on which the antenna is fabricated, with the blood vessel nominally at right angles to the direction of the antenna. For each configuration the heating power was calculated for two widths of blood vessels: 8 mm (FIGS. 12A and 13A) and 16 mm (FIGS. 12B and 13B). These are widths when flattened, which correspond to approximately 5 mm and 10 mm diameter blood vessels. In each case the centre of the blood vessel is the same distance along the antenna.

In FIGS. 12A and 12B, the coplanar microstrip antenna has a configuration similar to that described above with reference to FIGS. 6A and 6B, where a ground electrode forms a U-shape around a distal end of an elongate active electrode.

In FIGS. 13A and 13B, the coplanar microstrip antenna has a configuration similar to that described above with reference to FIGS. 7A and 7B, where a ground electrode and active electrode lie parallel in a longitudinal direction along the length of the jaw surface.

Each plot simulates power absorbed into the tissue when microwave energy having a frequency of 5.8 GHz and an input power of 0.5 W is applied from the coaxial antenna feed. A logarithmic shading scale is used to show the shape of both high power density and low power density regions.

In all of FIGS. 12A, 12B, 13A and 13B it can be seen that the power delivered is well constrained within a region 402 that corresponds to the width of the antenna. Very little power is delivered outside this region. Within the region 402 there is central strip having a power density of around 105 dB(mW/m$^3$), surrounding by a pair of side strips having a power density of around 95 dB(mW/m$^3$). With the central strip there are small zones 404, 406 of high power density, i.e. around 115 dB(mW/m$^3$). The units dB(mW/m$^3$) correspond to the logarithmic scale and indicate power density in decibels above 1 mW per cubic metre. These power densities and their equivalents are expressed in alternative units in Table 1.

TABLE 1 power density equivalents

| dB (mW/m$^3$) at 0.5 W | dB (mW/mm$^3$) at 1 W | W/mm$^3$ at 1 W | cal/cm$^3$ at 1 W |
| --- | --- | --- | --- |
| 115 | 28 | 0.65 | 151 |
| 105 | 18 | 0.065 | 15.1 |
| 95 | 8 | 0.0065 | 1.51 |

The last column shows power absorbed in calories per cubic cm. The calorie is defined as the heat required to increase the temperature of 1 gram of water by 1 degree Kelvin. To the accuracy useful in this treatment the heat capacity of 1 cubic cm of tissue is close to that of 1 gram of water, so the heat absorption in cal/cm$^3$ is close to the immediate rate of temperature rise in degrees per second.

The top value of heating density is equivalent to a rate of temperature rise of 151 K/s for 1 W input power. However, this is only possible over very small volumes as it requires a heat power density of 0.65 W/mm$^3$ which in turn would require 65% of the total available power to be focussed within a cubic mm.

The combined effects of heat capacity, heat conduction and perfusion mean that this rate of temperature rise does not actually happen except at the very instant when the power is switched on. In practice, for volumes of tissue of about one cubic millimetre the heating (i.e. rate of temperature rise) is ½ of the initial rate after 1 second and ⅓ after 2 seconds. For a volume with about 0.25 mm radius the heating is 1/6.5 of the initial rate after 1 second and 1/12 after 2 seconds.

In the plots shown in FIGS. 12a, 12B, 13A and 13B, the regions of highest power density are very small. For these regions the initial rate of temperature rise reduces rapidly with time. The temperature rise for any significant time should be estimated using average power density over regions several millimetres across. This average power density can be estimated to lie between 15.1 cal/cm$^3$/W at the 'hot' end and 1.51 cal/cm$^3$/W at the 'cold' end. This corresponds to a rate of heating between 15 K/s and 1.5 K/s for 1 W input power, and between 375 K/s and 37.5 K/s for 25 W input power.

The temperature will not rise continuously at this rate. The starting temperature is about 35° C. Between 45° C. and 60° C. extra power is required to denature tissue, which slightly slows the rate of rise, so that 60° C. would be reached in the time when it might be expected to be 65° C., and when the tissue reaches 100° C. the generation of water vapour will stop the temperature from rising for a time so that it will pass above 100° C. in the time that it would be expected to pass above 600° C.

This is summarised in the tables below:

TABLE 2

Behaviour for 1 W input power

| cal/cm$^3$ | K/s | Time to denature (s) | Time to vaporise (s) |
| --- | --- | --- | --- |
| 151 | 151 | 0.033 | 3.3 |
| 15.1 | 15.1 | 0.33 | 33 |
| 1.51 | 1.51 | 3.3 | 330 |

TABLE 3

Behaviour for 25 W input power

| cal/cm$^3$ | K/s | Time to denature (s) | Time to vaporise (s) |
| --- | --- | --- | --- |
| 3800 | 3800 | 0.0013 | 0.13 |
| 380 | 380 | 0.013 | 1.3 |
| 38 | 38 | 0.13 | 13 |

The generation and dispersal of hot water vapour from the hottest places will help to even out some of the power input and temperature difference across the device.

The variation in power density across the device is due to a number of factors. The transverse variation is because the microwave power is strongest beside the slots between the electrodes, particularly close to the edges of the slots, and much lower across the surface of the electrodes. In the configuration shown in FIGS. 12A and 12B, the heating is the same beside the slots on both sides of the central electrode, but in the configuration shown in FIGS. 13A and 13B, the heating is expected to be stronger in the gap between the two electrodes, and smaller on the other side of the active electrode (i.e. the conductive layer with no through holes in it).

The longitudinal variation is due to two factors, the efficiency of heating, coupled with the length of the tissue strip, and the reflection of power at the distal end of the tissue. Because the transmission line is uniform, the proportion of the power that is in the line that is coupled into the tissue over any length is constant. The power remaining in the line falls as the energy travels away from the feed because power has entered the tissue. The coupled power is a fixed proportion of the falling power remaining, so the heating reduces away from the feed to the tool.

In addition to this, there is always some power remaining at the end of the tissue. There is a reflection from the end of the tissue, and this reflection reinforces the heating for a short distance from the end. This results in a small dip in the heating away from the far end. The proportional change, relative to the heating at the end, does not depend on the length of the sample, so on the logarithmic display the shapes of the contours are similar for the different antenna configurations and for the different tissue lengths.

FIGS. 14A, 14B, 15A and 15B are charts showing the return loss of the antenna configurations shown in FIGS. 12A, 12B, 13A and 13B respectively, from DC to 10 GHz. The return loss is shown in dB, where 0 dB means all the signal is reflected (0% efficiency) and −20 dB means 1% is reflected (99% efficiency).

The table below gives the efficiency, and dB loss in heating, for a number of return loss values:

TABLE 4

Return loss comparison with efficiency

| Return loss (dB) | −3 | −4 | −6 | −7 | −10 | −20 |
|---|---|---|---|---|---|---|
| Efficiency (%) | 50% | 60% | 75% | 80% | 90% | 99% |
| Efficiency (dB) | −3.0 | −2.2 | −1.3 | −0.97 | −0.46 | −0.04 |

It can be seen from the table that even with a return loss of −6 dB the antenna still uses 75% of the power available, and the heating power reduction is only −1.3 dB. However, a return loss of −10 dB or better is preferable, with efficiency above 90% and a heating power loss no worse than −0.5 dB.

FIGS. 14A, 14B, 15A and 15B show the return loss with an 8 mm wide blood vessel. Simulations were also run to calculate return loss with a 16 mm wide blood vessel. In each case the return loss at 5.8 GHz was better for the 16 mm wide blood vessel than for the 8 mm wide blood vessel. The antenna is thus designed to be more efficient for the wider blood vessels. The efficiency for narrower blood vessels is never below −3 dB, so that in the examples tested the loss in power is always at least matched by the reduction in volume of tissue to be heated, so that the sealing time for narrower vessels should the same as or even quicker than the sealing time for wider vessels.

Figure 16A:
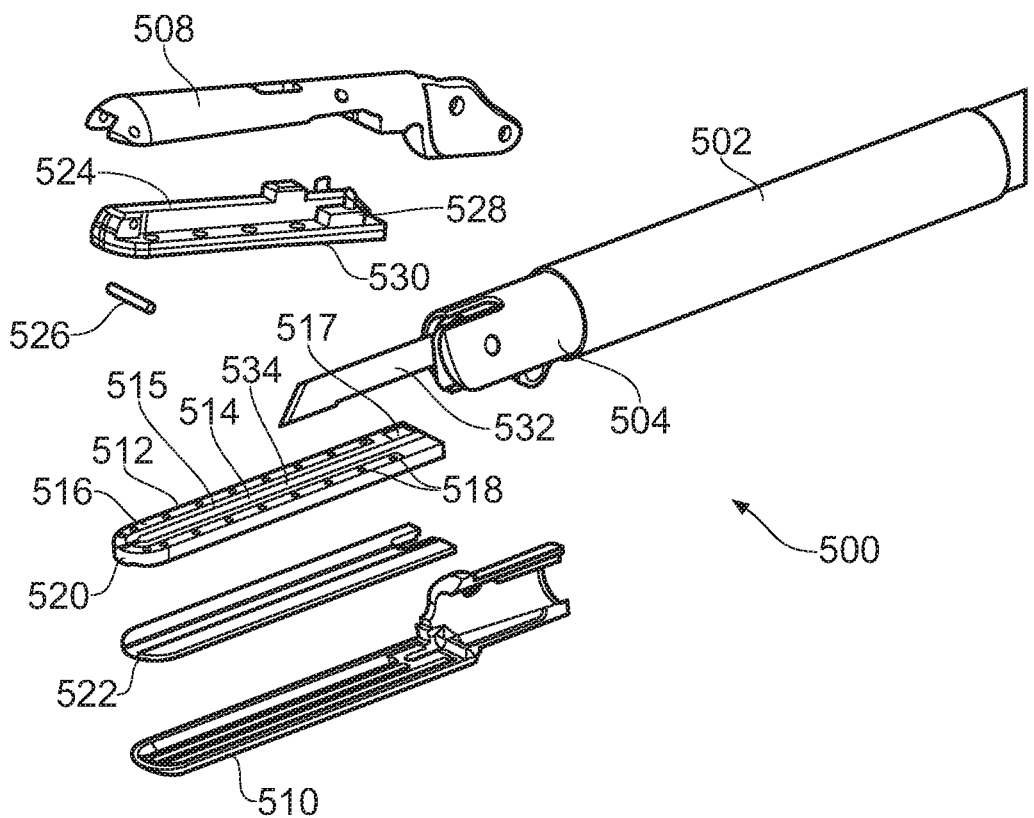
FIG. 16A is an exploded view of a distal tip assembly of an electrosurgical instrument that is another embodiment of the invention.

FIG. 16A is an exploded view of a distal tip assembly 500 for an electrosurgical invention that is another embodiment of the invention. The distal end assembly 500 is connected to an instrument shaft 502 which is dimensioned to fit within the instrument channel of a laparoscope or other surgical scoping device.

In this example, the distal end assembly 500 comprises a pair of jaws 508, 510. The jaws 508, 510 are operably coupled to a collar 504 that is mounted on a distal end of the instrument shaft 502. In this example, the pair of jaws 508, 510 comprise a movable jaw 508 which is pivotal around a laterally extending pin (not shown) in the collar 504 to enable a gap between opposing inner surfaces of the jaws 508, 510 to be opened and closed. The other jaw is a static jaw 510 that has an energy delivery structure 512 on its top surface, i.e. the surface that opposes a corresponding surface on the movable jaw 508. The collar 504 may be arranged to ensure that the jaws remain laterally aligned as they are moved together.

In use, the distal end assembly 500 is intended to grip biological tissues (and in particular a blood vessel) between the pair of jaws 508, 510. The pair of jaws 508, 510 are arranged to apply pressure to the biological tissue between the opposed surfaces and deliver energy (preferably microwave electromagnetic energy) into the tissue from the energy delivery structure 512.

In this example, the energy delivery structure 512 comprises a coplanar microstrip antenna mounted on a top surface of the status jaw 510. The coplanar microstrip antenna comprises a substrate 520 made of nonconductive dielectric material, e.g. ceramic or the like. The dielectric substrate 520 has a conductive layer fabricated on its underside. On its top surface (i.e. the surface opposite the underside) the dielectric substrate 520 has a first conductive region in the form of a longitudinally extending finger electrode 514 disposed centrally thereon. A U-shaped second conductive region 516 is disposed on the top surface of the dielectric substrate 520 around the finger electrode 514 with a gap of exposed dielectric 515 separating the finger electrode 514 from the U-shaped region 516. A plurality of through holes 518 are formed, e.g. machined, through the U-shaped region 516 and dielectric substrate 520. The through holes 518 are filled with conductive material to electrically connect the conductive layer on the underside of the dielectric substrate 520 with the U-shaped conductive region 516. The finger electrode 514 has a contact pad 517 at a proximal end thereof. An inner conductor of a coaxial cable conveyed by the instrument shaft 502 can be electrically coupled to the contact pad 517, e.g. by extending from the instrument shaft 502 to physically contact the contact pad 517. The finger electrode 514 thus provides an active region for the coplanar microstrip antenna. The conductive layer on the underside of the dielectric substrate 520 is electrically connected to an outer conductor of the coaxial cable conveyed by the instrument shaft 502. In conjunction with the conductive communication through the through holes 518, the U-shaped conductive region 516 forms a ground electrode for the coplanar microstrip antenna.

The static jaw 510 may comprise a body formed from a rigid material to provide structural support for the distal tip assembly. For example, it may be formed from metal, such as stainless steel. A barrier layer 522 is mounted between the substrate 520 and static jaw 510. The barrier layer 522 is made of a thermal and electrically insulating material, e.g. PEEK or the like. The barrier provides two functions. Firstly it isolates the antenna from the body of the static jaw 510, e.g. to inhibit or prevent leakage of microwave energy into the static jaw. Secondly, it provides a thermal barrier to inhibit or prevent heat conduction away from the antenna into the body of the static jaw. In combination, these features ensure that the available microwave energy transmitted from the antenna is focused where needed. This provides advantages in terms of improved control, reduced thermal margin, improved device efficiency, and reduction of the risk of collateral tissue damage caused by leaking thermal energy.

In this example, the movable jaw 508 comprising a body made of a rigid material, e.g. metal, such as stainless steel. Mounted within the body is a back hinge plate 524. The back hinge plate 524 is pivotally connected to the distal end of the movable jaw, e.g. on a pin 526 that is mounted in the movable jaw 508. The back hinge plate 524 is arranged to pivot into a recess formed by the body of the movable jaw 508.

A resiliently deformable cushion element 528 is mounted on a back surface of the back hinge plate 524 to engage the inside surface of the movable jaw 508 when the back hinge plate 524 pivots into the recess. The resiliently deformable cushion element 528 may be formed from silicone rubber or the like. The cushion element 528 acts as a spring that is compressible under load as the pair of jaws is closed around a vessel or tissue bundle. On loading in this way it reduces the angle of inclination between the jaws as they are closed, thereby helping improve jaw alignment and parallelism earlier as the jaws are clamped together. This improves the evenness of pressure distribution across the vessel as it is clamped and improves stability, e.g. helps prevent a slippery vessel or tissue bundle from moving distally during jaw closure.

The movable jaw 508 also has a layer of resiliently deformable material 530 formed on the underside of the back hinge plate 524, i.e. on the surface that is brought into contact with the antenna as the pair of jaws is closed. The layer 530 may be formed from silicone rubber or other compliant polymer material that can withstand the temperatures that occur during treatment and are biocompatible. They may be fabricated from an elastomeric thermoplastic polymer, for example. This layer both assists in efficient delivery of energy to gripped biological tissue, but also facilitates retaining the biological tissue within the jaws.

The distal tip assembly 500 further comprises a blade 532 that is slidably mounted with respect to the pair of jaws 508, 510 to cut through biological tissue held between the jaws. The blade 532 is movable in a longitudinal direction, e.g. along the axis of the device. The opposed surfaces of the jaws 508, 510 contain respective recess or guide grooves 534 for receiving the blade as it travels. The guide groove 534 in the static jaw 510 is formed within the finger electrode 514 so that is moves through the centre of the applied field.

Although not shown in FIG. 16A, the distal tip assembly 500 may also comprise an auxiliary radiofrequency (RF) cutting blade mounted on a distal tip thereon, in a similar manner to that discussed above.

Figure 16B:
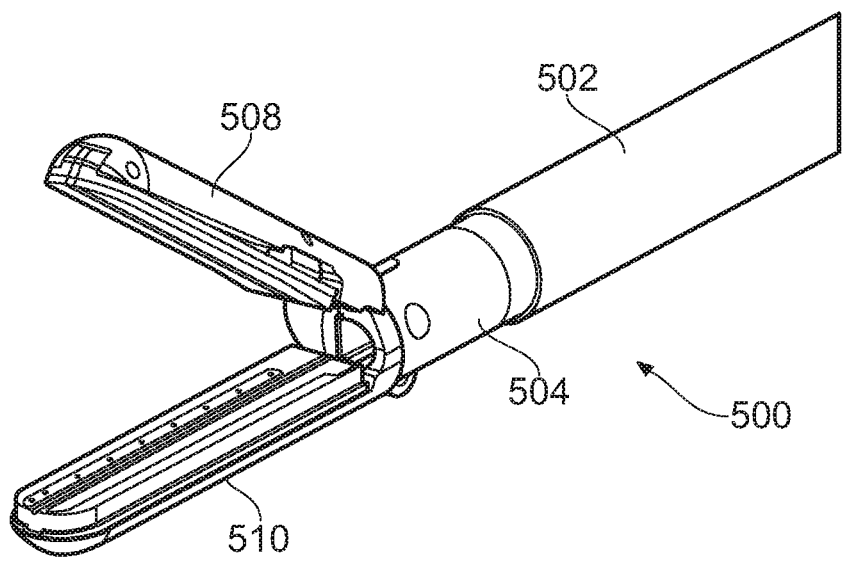
FIG. 16B is a perspective view of the distal tip assembly of FIG. 16A when assembled.

FIG. 16B is a perspective view of the distal tip assembly 500 of FIG. 16A when assembled.

Figures 17A, 17B, 17C:
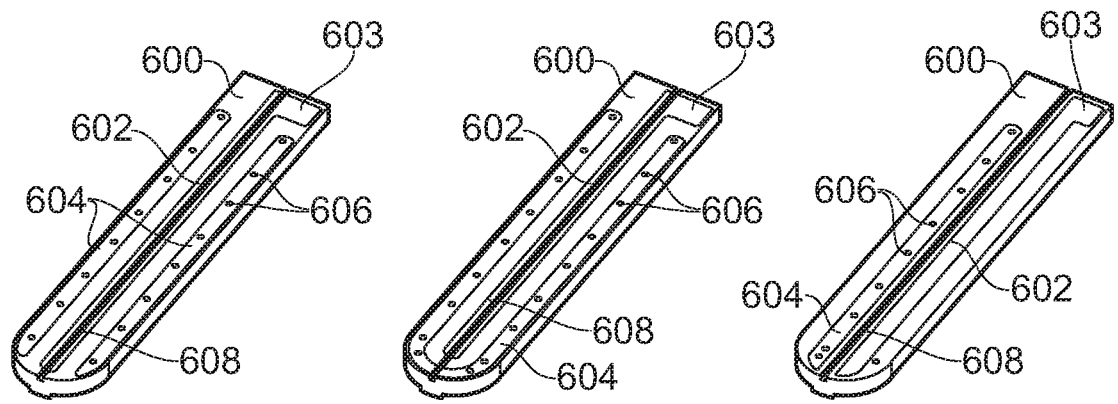
FIGS. 17A, 17B and 17C show three example coplanar microstrip antennas that can be used in an electrosurgical instrument that is an embodiment of the invention.

FIGS. 17A, 17B and 17C show three further examples of a coplanar microstrip antenna configuration that can be provided on the upper surface of the static jaws in the embodiments discussed above. In each example, the coplanar microstrip antenna comprises a substrate 600 having an underside (not shown) that has a ground electrode formed thereon and an upper side from which energy can be delivered. An elongate active electrode 602 is formed as a strip along the upper side. At a proximal end of the active electrode 602 a contact pad 603 is formed to connect to an inner conductor of a coaxial feed, as discussed above. An elongate return electrode 604 is formed adjacent the active electrode 602. The return electrode 604 is electrically connected to the ground electrode on the underside of the substrate 600 through vias 606 formed through the substrate 600. An elongate slot 608 is provided in the substrate to facilitate passage of the sliding blade as discussed above. The electrodes 602, 604 may be formed on the substrate using any suitable technique, e.g. metallisation, thin film deposition and patterning (etching), etc.

In the first example shown in FIG. 17A, the slot 608 is formed down the centre of the active electrode 602. The return electrode 604 comprises a pair of separate strips formed on either side of the active electrode. The active electrode 604 extends to the distal end of the substrate.

The second example shown in FIG. 17B is similar to the first example, except that the active electrode 602 is set back from the distal end of the substrate and the pair of strips forming the return electrode are joined by a curved section that passes around a curved distal edge of the substrate. The return electrode therefore provides a single U-shaped element.

In the third example shown in FIG. 17C, the active electrode 602 and return electrode are located on opposite sides of the slot, and each comprise a single elongate finger electrode.

Figure 18:
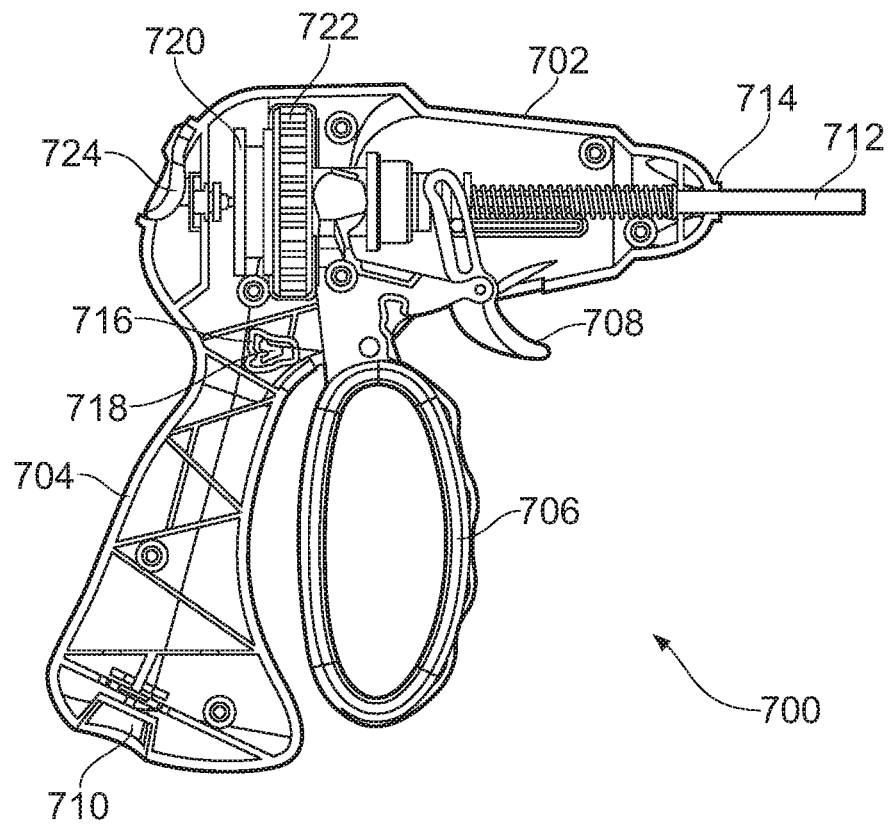
FIG. 18 is a cross-sectional view of a handle that can be used to operate an electrosurgical instrument that is an embodiment of the invention.

FIG. 18 is a cross-sectional view of a handle 700 that can be used to operate an electrosurgical instrument that is an embodiment of the invention. The handle 700 comprises a body 702 with a handgrip 704 and a pair of trigger-type actuators 706, 708. An input port 710 for receiving a microwave energy supply is provided on a base of the handgrip 704. The body 702 includes an output port 714 to which an instrument shaft 712 is mounted.

Closure of the pair of jaws at the distal tip assembly is effected by a grip actuator 706. Pulling the grip actuator 706 towards the handgrip 704 causes axial movement of a closure sleeve forward along the instrument shaft 712 thereby causing the jaws to close. The mode of actuation is desirable compared with retraction. Retraction typically causes the device to move away from the target tissue at the distal end of the instrument shaft, which means there is a risk that the tissue will slip out from between the jaw faces. The grip actuator 706 may be latched in position by means of a latch racetrack formed within the body 702, which receives an engagement element 718 that protrudes rearwardly from the grip actuator 706.

Movement of the blade within the distal tip assembly is effected by a blade actuator 708, which is mounted on the grip actuator 706 in a compound hinge arrangement. This arrangement can be configured such that the blade trigger remains hidden in the body 702 until the jaws are closed to the required extent.

Microwave energy is conveyed to the distal tip assembly by a coaxial cable that extends from the input port 710 through the instrument shaft 712. The body includes a rotatable spool 720 around which the coaxial cable is wound a number of time (e.g. 2 or 3 times) before as part of its routing from the input port 710 to the instrument shaft 712. These cable rotations allow free rotation of the shaft and distal tip assembly through 360° (+/−180°) via a thumb wheel 722 that is rotatably mounted in the body 702. This arrangement reduces the resistance load when rotating the shaft, and can avoid sharp bends or stress points within the coaxial cable.

The body 702 further comprises an energy activation push button 724 that enables control over the delivery of microwave energy when the device is in use.

In use, the device may be arranged to deliver continuous microwave energy having a predetermined power for a certain duration selected to effect delivery of a required amount of energy. For example, if it was desirable to deliver 100 J of energy, the device may be arranged to supply power at 25 W for 4 seconds.

However, instead of delivering continuous energy at a constant power, it has been found that delivering energy as discrete pulses is more effective, particular with larger vessel sizes. For example, 100 J may be delivered as a pair of 1 second pulses at 50 W separated by off time of 2 seconds. The power level of the pulse may be in a range from 50 W to 60 W. The pulse duration may be in a range from 0.5 second to 1 second. The rest period may be in a range from 0.5 second to 2 second. The pulses may be identical, or the first pulse may have a higher power level. The duration and overall energy delivery may be selected depending on the vessel size or tissue bundle (containing multiple vessels) being sealed. The energy may be deliver in a pulse train that comprises more than two pulses, e.g. with the power level of each pulse ramping down through the treatment period. For example, in a treatment period of 5 seconds, 6 energy pulses may be delivered. The first energy pulse may be at 60 W for 1 second, followed by 5 shorter pulses of steadily decreasing power.

The vessel sealer device and apparatus discussed above may find application is a very wide variety of procedures. It is likely to find particular use in open and laparoscopic surgery of the gastrointestinal tract, and may also be useful in colorectal surgery.

More generally, the device and apparatus may find use in open, laparoscopic and minimally invasive procedures relating to gynaecological surgery, urological surgery, hepatobiliary surgery, endocrine surgery, plastic, cosmetic and reconstructive surgery, orthopaedic surgery, thoracic surgery and cardiac surgery. The device is suitable for use in adult, paediatric and veterinary procedures.

REFERENCES

[1] Presthus, et al.: Vessel sealing using a pulsed bipolar system and open forceps, *J Am Assoc Gynecol Laparosc* 10(4):528-533, 2003.
[2] Carbonell, et al.: A comparison of laparoscopic bipolar vessel sealing devices in the hemostasis of small-, medium-, and large-sized arteries, J Laparoendosc Adv Surg Tech 13(6):377-380, 2003
[3] Richter, et al.: Efficacy and quality of vessel sealing, *Surg Endosc* (2006) 20: 890-894

The invention claimed is:

1. An electrosurgical vessel sealer comprising: an instrument shaft comprising a coaxial transmission line for conveying microwave electromagnetic (EM) energy;
a distal end assembly arranged at a distal end of the instrument shaft to receive the microwave EM energy from the instrument shaft, the distal end assembly comprising:
a pair of jaws that are movable relative to each other to open and close a gap between opposing inner surfaces thereof; and
a blade for cutting through biological tissue, wherein the pair of jaws comprise an energy delivery structure arranged to emit the microwave EM energy into the gap between the opposing inner surfaces,
wherein the blade is slidably disposed within the distal end assembly to be movable through the region between the pair of jaws, and
wherein the energy delivery structure comprises a coplanar microstrip antenna mounted on the inner surface of one or both of the pair of jaws, the coplanar microstrip antenna being arranged to confine an emitted microwave field substantially within a region between the pair of jaws, and
wherein the coplanar microstrip antenna comprises:
a planar dielectric substrate having a top surface that is exposed at the gap between the opposing inner surfaces, and an under surface on an opposite side of the planar dielectric substrate from the top surface;
a ground conductor layer on the under surface;
a ground conductive strip on the top surface and electrically connected to the ground conductor layer; and
an active conductive strip on the top surface, the active conductive strip being spaced from the ground conductive strip, and
wherein the ground conductor layer overlaps a portion of the under surface that is diametrically opposed from the ground conductive strip and a portion of the under surface that is diametrically opposed from the active conductive strip.

2. An electrosurgical vessel sealer according to claim 1, wherein the active conductive strip and the ground conductive strip are positioned to have a uniform closest spacing within the region between the pair of jaws.

3. An electrosurgical vessel sealer according to claim 2, wherein the active conductive strip is an elongate longitudinally extending finger electrode, and wherein the ground conductive strip is a U-shaped element that flanks the finger electrode and surrounds its distal end.

4. An electrosurgical vessel sealer according to claim 2, wherein the ground conductive strip is electrically connected to the ground conductor layer via through holes formed in the dielectric substrate.

5. An electrosurgical vessel sealer according to claim 1, wherein the pair of jaws comprises an active jaw having the energy delivery structure mounted therein, and a passive jaw which does not receive a microwave EM energy feed, wherein the inner surface of the passive jaw at the gap comprises a resilient deformable layer of electrically insulating material.

6. An electrosurgical vessel sealer according to claim 1, wherein the opposing inner surfaces include textured or ridged portions to retain biological tissue within the gap.

7. An electrosurgical vessel sealer according to claim 1, wherein the pair of jaws comprises:
a static jaw that is fixed relative to the instrument shaft, and
a movable jaw that is pivotably mounted relative to the static jaw to open and close the gap between the opposing inner surfaces.

8. An electrosurgical vessel sealer according to claim 7, wherein the energy delivery structure is disposed on the inner surface of the static jaw.

9. An electrosurgical vessel sealer according to claim 1, wherein the blade is a slidable in a longitudinal direction along a longitudinally extending recessed groove between a retracted position in which it lies proximal to the pair of jaws and an extended position in which it lies within the region between the pair of jaws.

10. An electrosurgical vessel sealer according to claim 1, wherein the instrument shaft is arranged to convey radiofrequency (RF) EM energy and the distal end assembly is arranged to receive the RF EM energy from the instrument shaft, and wherein the distal end assembly further comprises a dissector element arranged to deliver the RF EM energy for cutting through biological tissue, wherein the dissector element is located outside the region between the pair of jaws.

11. An electrosurgical vessel sealer according to claim 1, wherein the active conductive strip is an elongate longitudinally extending finger electrode, and wherein the ground conductive strip flanks the finger electrode on at least two sides.

12. An electrosurgical vessel sealer comprising:
an instrument shaft arranged to convey microwave electromagnetic (EM) energy and radiofrequency (RF) EM energy;
a distal end assembly arranged at a distal end of the instrument shaft to receive the microwave EM energy and the RF EM energy from the instrument shaft, the distal end assembly comprising:
a pair of jaws that are movable relative to each other to open and close a gap between opposing inner surfaces thereof; and
a dissector element arranged to deliver the RF EM energy for cutting through biological tissue,
wherein the pair of jaws comprise an energy delivery structure arranged to emit the microwave EM energy into the gap between the opposing inner surfaces,
wherein the energy delivery structure is arranged to confine an emitted microwave field substantially within a region between the pair of jaws,
wherein the energy delivery structure comprises a coplanar microstrip antenna mounted on the inner surface of one or both of the pair of jaws, the coplanar microstrip antenna being arranged to confine an emitted microwave field substantially within a region between the pair of jaws,
wherein the coplanar microstrip antenna comprises:
a planar dielectric substrate having a top surface that is exposed at the gap between the opposing inner surfaces, and an under surface on an opposite side of the planar dielectric substrate from the top surface;
a ground conductor layer on the under surface;
a ground conductive strip on the top surface and electrically connected to the ground conductor layer; and
an active conductive strip on the top surface, the active conductive strip being spaced from the ground conductive strip, and
wherein the ground conductor layer overlaps a portion of the under surface that is diametrically opposed from the ground conductive strip and a portion of the under surface that is diametrically opposed from the active conductive strip, and
wherein the dissector element is located outside the region between the pair of jaws and comprises a protruding body mounted at a distal end of the distal end assembly.

13. An electrosurgical vessel sealer according to claim 12, wherein the dissector element comprises a bipolar RF structure having an active electrode and a return electrode.

14. An electrosurgical vessel sealer according to claim 13, wherein the protruding body presents a leading edge for contacting tissue, and wherein the active electrode is provided at the leading edge.

15. An electrosurgical vessel sealer according to claim 12, wherein the dissector element is mounted on an outer surface of the pair of jaws.

16. An electrosurgical vessel sealer according to claim 12, wherein the dissector element is mounted on a longitudinal extender, the longitudinal extender being movable longitudinally with respect to the pair of jaws.

17. An electrosurgical vessel sealer according to claim 12, wherein the instrument shaft comprises a coaxial transmission line that provide a common signal pathway for conveying both the microwave EM energy and the RF EM energy, and wherein the distal end assembly comprises an inductive filter for blocking the microwave EM energy from the dissector element, and a capacitive filter for blocking the RF EM energy from the energy delivery structure on the pair of jaws.

18. An electrosurgical vessel sealer according to claim 12, wherein the distal end assembly and instrument shaft are dimensioned to fit within an instrument channel of a surgical scoping device.

19. An electrosurgical vessel sealer comprising:
an instrument shaft comprising a coaxial transmission line for conveying microwave electromagnetic (EM) energy;
a distal end assembly arranged at a distal end of the instrument shaft to receive the microwave EM energy from the instrument shaft, the distal end assembly comprising:
a pair of jaws that are movable relative to each other to open and close a gap between opposing inner surfaces thereof; and
a blade for cutting through biological tissue,
wherein the pair of jaws comprise an energy delivery structure arranged to emit the microwave EM energy into the gap between the opposing inner surfaces,
wherein the blade is slidably disposed within the distal end assembly to be movable through the region between the pair of jaws, and
wherein the energy delivery structure comprises a coplanar microstrip antenna mounted on the inner surface of one or both of the pair of jaws, the coplanar microstrip antenna being arranged to confine an emitted microwave field substantially within a region between the pair of jaws,
wherein the coplanar microstrip antenna comprises:
a planar dielectric substrate having a top surface that is exposed at the gap between the opposing inner surfaces, and an under surface on an opposite side of the planar dielectric substrate from the top surface;
a ground conductor layer on the under surface,
a ground conductive strip on the top surface and electrically connected to the ground conductor layer; and
an active conductive strip on the top surface, the active conductive strip being spaced from the ground conductive strip,
wherein the ground conductor layer extends to a proximal-most end and a distal-most end of the planar dielectric substrate.

20. An electrosurgical vessel sealer according to claim 18, wherein the surgical scoping device is a laparoscope.

21. An electrosurgical vessel sealer comprising:
an instrument shaft arranged to convey microwave electromagnetic (EM) energy and radiofrequency (RF) EM energy;
a distal end assembly arranged at a distal end of the instrument shaft to receive the microwave EM energy and the RF EM energy from the instrument shaft, the distal end assembly comprising:
a pair of jaws that are movable relative to each other to open and close a gap between opposing inner surfaces thereof; and
a dissector element arranged to deliver the RF EM energy for cutting through biological tissue,
wherein the pair of jaws comprise an energy delivery structure arranged to emit the microwave EM energy into the gap between the opposing inner surfaces,
wherein the energy delivery structure is arranged to confine an emitted microwave field substantially within a region between the pair of jaws,
wherein the energy delivery structure comprises a coplanar microstrip antenna mounted on the inner surface of one or both of the pair of jaws, the coplanar microstrip antenna being arranged to confine an emitted microwave field substantially within a region between the pair of jaws,
wherein the coplanar microstrip antenna comprises:
a planar dielectric substrate having a top surface that is exposed at the gap between the opposing inner surfaces, and an under surface on an opposite side of the planar dielectric substrate from the top surface;
a ground conductor layer on the under surface;
a ground conductive strip on the top surface and electrically connected to the ground conductor layer; and
an active conductive strip on the top surface, the active conductive strip being spaced from the ground conductive strip, and
wherein the ground conductor layer extends to a proximal-most end and a distal-most end of the planar dielectric substrate, and wherein the dissector element is located outside the region between the pair of jaws and comprises a protruding body mounted at a distal end of the distal end assembly.

* * * * *